US011207455B2

(12) United States Patent
Remcho et al.

(10) Patent No.: US 11,207,455 B2
(45) Date of Patent: Dec. 28, 2021

(54) MEMBRANE DEVICE FOR BLOOD SEPARATION AND METHODS OF MAKING AND USING THE SAME

(71) Applicant: Oregon State University, Corvallis, OR (US)

(72) Inventors: Vincent T. Remcho, Corvallis, OR (US); Gayan C. Bandara, Portland, OR (US); Linus Jacob Unitan, Corvallis, OR (US); Matthew H. Kremer, Philomath, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 16/809,312

(22) Filed: Mar. 4, 2020

(65) Prior Publication Data
US 2020/0197593 A1 Jun. 25, 2020

Related U.S. Application Data

(63) Continuation-in-part of application No. 16/410,637, filed on May 13, 2019, now abandoned.
(Continued)

(51) Int. Cl.
*A61M 1/34* (2006.01)
*B01D 63/08* (2006.01)
(Continued)

(52) U.S. Cl.
CPC ......... *A61M 1/3403* (2014.02); *B01D 63/087* (2013.01); *B01D 71/48* (2013.01);
(Continued)

(58) Field of Classification Search
CPC ........ A61M 1/3403; A61M 2205/3331; B01D 63/087; B01D 71/48; B01D 2325/38;
(Continued)

(56) References Cited

U.S. PATENT DOCUMENTS 3,730,807 A 5/1973 Smith et al.
8,628,729 B2 1/2014 Carrilho et al.
(Continued)

FOREIGN PATENT DOCUMENTS

CN 105548315 A 5/2016
EP 2016189 B1 * 1/2012 ........... C12Q 1/6869
(Continued)

OTHER PUBLICATIONS

Guarino et al. (V Guarino, G Gentile, L Sorrentino, L Ambrosio, Polycaprolactone: synthesis, properties and applications, Encyclopedia of Polymer Science and Technology, John Wiley & Sons, DOI: 10.1002/0471440264.pst658; published online Aug. 15, 2017) (Year: 2017).*

(Continued)

*Primary Examiner* — Joshua L Allen
(74) *Attorney, Agent, or Firm* — Klarquist Sparkman, LLP

(57) ABSTRACT

Disclosed herein are membrane device embodiments that can be used for separating blood plasma and/or blood serum from blood samples. The membrane device embodiments comprise built-in features that facilitate blood plasma and/or blood serum separation and also provide the ability to detect, quantify, and qualify analytes present in a blood sample. The membrane device embodiments are portable and just a single membrane can be used for a plethora of detection and analysis techniques. Also disclosed herein are embodiments of methods for making and using the membrane device.

17 Claims, 18 Drawing Sheets

Related U.S. Application Data

(60) Provisional application No. 62/671,281, filed on May 14, 2018, provisional application No. 62/847,064, filed on May 13, 2019, provisional application No. 62/849,636, filed on May 17, 2019.

(51) Int. Cl.
　　*B01D 71/48* (2006.01)
　　*G01N 33/49* (2006.01)

(52) U.S. Cl.
　　CPC ..... *G01N 33/49* (2013.01); *A61M 2205/3331* (2013.01); *B01D 2313/10* (2013.01); *B01D 2325/36* (2013.01); *B01D 2325/38* (2013.01)

(58) Field of Classification Search
　　CPC ............ B01D 2313/10; B01D 2325/36; B01D 63/088; G01N 33/49
　　See application file for complete search history.

(56) References Cited

U.S. PATENT DOCUMENTS

| | | |
|---|---|---|
| 2003/0102080 A1 | 6/2003 | Mallik |
| 2003/0220700 A1 | 11/2003 | Hammer et al. |
| 2004/0037990 A1 | 2/2004 | Abe et al. |
| 2004/0053422 A1* | 3/2004 | Chan ................ B01L 3/502753 436/180 |
| 2008/0099064 A1 | 5/2008 | Hayes |
| 2009/0181411 A1 | 7/2009 | Battrell et al. |
| 2011/0011781 A1* | 1/2011 | Blankenstein ......... B01D 29/05 210/205 |
| 2011/0135698 A1* | 6/2011 | Lundquist ............ C12N 5/0644 424/400 |
| 2011/0107168 A1 | 8/2011 | Kornev et al. |
| 2011/0272644 A1 | 11/2011 | Remcho et al. |
| 2013/0064713 A1* | 3/2013 | Koesdjojo ......... B01L 3/502738 422/69 |
| 2013/0146643 A1 | 6/2013 | Schmid et al. |
| 2014/0106139 A1 | 4/2014 | Abrams |
| 2014/0235510 A1 | 8/2014 | Chang-Yen et al. |
| 2014/0248471 A1 | 9/2014 | Hanschen et al. |
| 2016/0146823 A1* | 5/2016 | Chiu ................... G01N 15/1456 506/9 |
| 2016/0158428 A1* | 6/2016 | Charest ............... A61M 1/3403 210/637 |
| 2018/0178212 A1* | 6/2018 | Roxhed ............ B01L 3/502738 |
| 2018/0200677 A1* | 7/2018 | Lee .................. A61B 5/150358 |
| 2018/0353956 A1 | 12/2018 | Bandara et al. |
| 2019/0091688 A1 | 3/2019 | Bandara et al. |
| 2019/0242870 A1* | 8/2019 | Doi ........................ G01N 33/48 |

FOREIGN PATENT DOCUMENTS

| | | |
|---|---|---|
| WO | WO 2011/072715 | 6/2011 |
| WO | WO 2011/097677 | 8/2011 |
| WO | WO 2012/071629 | 6/2012 |
| WO | WO 2016/172675 | 10/2016 |
| WO | WO 2016/209147 | 12/2016 |
| WO | WO 2017/210199 | 12/2017 |

OTHER PUBLICATIONS

Jenkins et al. (MJ Jenkins, KL Harrison, The effect of molecular weight on the crystallization kinetics of polycaprolactone, Polym. Adv. Technol. 17 (2006) 474-478) (Year: 2006).*

Jayawardane et al. (BM Jayawardane, L Coo, RW Cattrall, SD Kolev, The use of a polymer inclusion membrane in a paper-based sensor for the selective determination of Cu, Analytica Chimica Acta 803 (2013) 106-112) (Year: 2013).*

"Paper Microzone Plates," NIH 3D Print Exchange: A collection of biomedical 3D printable files and 3D printing resources supported by the National Institutes of Health, accessed at https://3dprint.nih.gov/discover/paper-microzone, Jul. 2014.

Abgrall et al., "Fabrication of planar nanofluidic channels in a thermoplastic by hot-embossing and thermal bonding," *Lab Chip*, No. 4, pp. 520-522, Jan. 11, 2007.

Allo et al., "Synthesis and Electrospinning of ε-Polycapralactone-Bioactive Glass Hybrid Biomaterials via a Sol-Gel Process," *Langmuir*, 26(23): 18340-18348, Nov. 4, 2010.

Armani et al., "Microfabrication technology for polycaprolactone, a biodegradable polymer," *J. Micromech. Microeng.*, 10(1): 80-84, Jan. 6, 2000.

Becker et al., "Hot embossing as a method for the fabrication of polymer high aspect ratio structures," *Sensors and Actuators*, 83(1-3): 130-135, May 22, 2000.

Burgoyne, "Interfacing of microfluidic devices." *Chips and Tips*, Feb. 27, 2009. rsc.org, blog, downloaded Jun. 27, 2013.

Carrilho et al., "Paper Microzone Plates," *Anal. Chem.*, 81(15): 5990-5998, Jul. 2, 2009.

Chen et al., "Fabrication, modification, and application of poly(methyl methacrylate) microfluidic chips," *Electrophoresis*, 29(9): 1801-1814, May 9, 2008.

Chen et al., "Vacuum-assisted thermal bonding of plastic capillary electrophoresis microchip imprinted with stainless steel template," *Journal of Chromatography A*, 1038(1-2): 239-245, Jun. 4, 2004.

Cheow et al., "Antibacterial Efficacy of Inhalable Antibiotic-Encapsulated Biodegradable Polymeric Nanoparticles Against *E. coli* Biofilm Cells," *Journal of Biomedical Nanotechnology*, 6(4): 391-403, Aug. 2010.

Christensen et al., "Characterization of interconnects used in PDMS microfluidic systems," *Journal of Micromechanics and Microengineering*, 15(5): 928-934, Mar. 22, 2005.

Chu et al., "Comparison of polyurethane foam and biodegradable polymer as carriers in moving bed biofilm reactor for treating wastewater with a low C/N ratio," *Chemosphere*, 83(1): 63-68, Mar. 2011.

Dang et al., "Replica multichannel polymer chips with a network of sacrificial channels sealed by adhesive printing method," *Lab Chip*, vol. 4, pp. 472-478, Feb. 1, 2005.

Davis et al., "Carrier systems and biosensors for biomedical applications," *Tissue Engineering Using Ceramics and Polymers: Second Edition*, pp. 270-302, 2014.

Esch et al., "Influence of master fabrication techniques on the characteristics of embossed microfluidic channels," *Lab Chip*, vol. 3, pp. 121-127, May 2, 2003.

Hu et al., "The use of reactive polymer coatings to facilitate gene delivery from poly (ε-caprolactone) scaffolds," *Biomaterials*, 30(29): 5785-5792, Oct. 2009.

International Search Report and Written Opinion issued for International Application No. PCT/US2017/35018 dated Oct. 3, 2017.

Ishida et al., "Reversed-phase liquid chromatography on a microchip with sample injector and monolithic silica column," *Journal of Chromatography A*, 1132(1-2): 90-98, Nov. 3, 2006.

Jacobson et al., "Effects of Injection Schemes and Column Geometry on the Performance of Microchip Electrophoresis Devices," *Anal. Chem.*, 66(7): 1107-1113, Apr. 1994.

Jain et al., "Performance of an Optimized Paper-Based Test for Rapid Visual Measurement of Alanine Aminotransferase (ALT) in Fingerstick and Venipuncture Samples," *PLOS ONE*, 10(5): 1-15, May 28, 2015.

Jayawardane et al., "The use of a polymer inclusion membrane in a paper-based sensor for the selective determination of Cu(II)," *Analytica Chimica Acta*, vol. 803, pp. 106-112, Nov. 25, 2013.

Kaigala et al., "Rapid prototyping of microfluidic devices with a wax printer," *Lab Chip*, vol. 7, pp. 384-387, Jan. 10, 2007.

Kelly et al., "Thermal Bonding of Polymeric Capillary Electrophoresis Microdevices in Water," *Anal. Chem.*, 75(8): 1941-1945, Apr. 15, 2003.

Khang et al., "Room-temperature imprint lithography by solvent vapor treatment," *Applied Physics Letters*, 76(7): 870-871, Feb. 4, 2000.

(56) References Cited

OTHER PUBLICATIONS

Kho et al., "Aqueous re-dispersibility of spray-dried antibiotic-loaded polycaprolactone nanoparticle aggregates for inhaled antibiofilm therapy," *Powder Technology*, 203(3): 432-439, Nov. 25, 2010.

Koesdjojo et al., "Fabrication of a Microfluidic System for Capillary Electrophoresis Using a Two-Stage Embossing Technique and Solvent Welding on Poly(methyl methacrylate) with Water as a Sacrificial Layer," *Anal. Chem.*, 80(7): 2311-2318, Apr. 1, 2008.

Koesdjojo et al., "Two-stage polymer embossing of co-planar microfluidic features for microfluidic devices," *Sensors and Actuators B*, 131(2): 692-697, May 14, 2008.

Kundu et al., "Continuous Flow Enzyme-Catalyzed Polymerization in a Microreactor," *JACS*, 133(15): 6006-6011, Mar. 25, 2011.

Lai et al., "A Packaging Technique for Polymer Microfluidic Platforms," *Anal. Chem.*, 76(4): 1175-1183, Feb. 15, 2004.

Lee et al., "Microfabricated plastic chips by hot embossing methods and their applications for DNA separation and detection," *Sensors and Actuators B*, vol. 75, pp. 142-148, 2001.

Lei et al., "Microwave bonding of polymer-based substrates for potential encapsulated micro/nanofluidic device fabrication," *Sensors and Actuators A*, 114(2-3): 340-346, Feb. 28, 2004.

Li et al., "Polydimethylsioxane Fluidic Interconnects for Microfluidic Systems," *IEEE Transactions on Advanced Packaging*, 26(3): 242-247, Aug. 2003.

Licata et al., "How to bond polycarbonate parts by solvent welding," *Plastics Engineering*, 42(6): 53-55, Jun. 1986.

Lim et al., "Micropatterning and Characterization of Electrospun Poly($\epsilon$-Caprolactone)/Gelatin Nanofiber Tissue Scaffolds by Femtosecond Laser Ablation for Tissue Engineering Applications," *Biotechnology and Bioengineering*, 108(1): 116-126, Jan. 1, 2011.

Lin et al., "Low azeotropic solvent for bonding of PMMA microfluidic devices," *Sensors and Actuators B*, 121(2): 698-705, Jun. 2, 2006.

Liu et al., "Fabrication of Balloon-Expandable Self-Lock Drug-Eluting Polycaprolactone Stents Using Micro-Injection Molding and Spray Coating Techniques," *Annals of Biomedical Engineering*, 38(10): 3185-3194, May 22, 2010.

Machell et al., "Optical Properties of Solvent-Cast Polymer Films," *Macromolecules*, 23(1): 186-194, 1990.

Manz et al., "Micromachining of monocrystalline silicon and glass for chemical analysis systems: A look into next century's technology or just a fashionable craze?," *Trends in Analytical Chemistry*, 10(5): 144-149, 1991.

Martinez et al., "Diagnostics for the Developing World: Microfluidic Paper-Based Analytical Devices," *Anal. Chem.*, 82(1): 3-10, Jan. 1, 2010.

Martinez et al., "Three-dimensional microfluidic devices fabricated in layered paper and tape," *PNAS*, 105(50): 19606-19611, Dec. 16, 2008.

McDonald et al., "Fabrication of microfluidic systems in poly(dimethylsiloxane)," *Electrophoresis*, 21 (1): 27-40, Jan. 1, 2000.

Muck, Jr. et al., "Fabrication of Poly(methyl methacrylate) Microfluidic Chips by Atmospheric Molding," *Anal. Chem.*, 76(8): 2290-2297, Feb. 28, 2004.

Peeni et al., "Sacrificial layer microfluidic device fabrication methods," *Electrophoresis*, 27(24): 4888-4895, Dec. 2006.

Pengumkiat et al., "A Paper-Based Disposable Well-Plate for Cyanide Detection Incorporating a Fluorescent Chitosan-CdTe Quantum Dot Nanoparticle," Abstract, PITTCON Conference and Expo 2017, Chicago, Mar. 2017.

Rella et al., "Rapid Cyanide Detection Using the Cyantesmo® Kit," *Journal of Toxicology, Clinical Toxicology*, 42(6): 897-900, 2004.

Roberts et al., "UV-Laser Machined Polymer Substrates for the Development of Micro-Diagnostic Systems," *Anal. Chem.*, 69(11): 2035-2042, Jun. 1, 1997.

Rossier et al., "Electrochemical Detection in Polymer Microchannels," *Anal. Chem.*, 71(19): 4294-4299, Oct. 1, 1999.

Rossier et al., "Electrophoresis with electrochemical detection in a polymer microdevice," *Journal of Electroanalytical Chemistry*, 492(1): 15-22, Sep. 29, 2000.

Rossier et al., "Topography, Crystallinity and Wettability of Photoablated PET Surfaces," *Langmuir*, 15(15): 5173-5178, Jun. 25, 1999.

Rundel et al., "Organic solvent nanofiltration for microfluidic purification of poly(amidoamine) dendrimers," *Journal of Chromatography A*, 1162(2): 167-174, Aug. 31, 2007.

Santiago et al., "Peptide-surface modification of poly(caprolactone) with laminin-derived sequences for adipose-derived stem cell applications," *Biomaterials*, 27(15): 2962-2969, Jan. 30, 2006.

Sarasam et al., "Characterization of chitosan-polycapralactone blends for tissue engineering applications," *Biomaterials*, 26(27): 5500-5508, Apr. 7, 2005.

Shah et al., "Capillarity Induced Solvent-Actuated Bonding of Polymeric Microfluidic Device," *Anal. Chem.*, 78(10): 3348-3353, Apr. 12, 2006.

Skotak et al., "Letter to the Editor," *Carbohydrate Polymers*, vol. 5, 1-3, Nov. 5, 2010.

Sousa et al., "Selective Protein Adsorption on a Phase-Separated Solvent-Cast Polymer Blend," *Langmuir*, 22(14): 6286-6292, May 28, 2006.

Sun et al., "Rapid Prototyping of Poly(methyl methacrylate) Microfluidic Systems Using Solvent Imprinting and Bonding," *J. Chromatogr. A*, 1162(2): 162-166, Aug. 31, 2007.

Wang et al., "Towards disposable lab-on-a-chip: Poly(methylmethacrylate) microchip electrophoresis device with electrochemical detection," *Electrophoresis*, 23(4): 596-601, Feb. 4, 2002.

Woodruff et al., "The return of a forgotten polymer—Polycaprolactone in the 21$^{st}$ century," *Progress in Polymer Science*, 35(10): 1217-1256, Apr. 7, 2010.

Xie et al., "Gas sensor arrays based on polymer-carbon black to detect organic vapors at low concentration," *Sensors and Actuators B*, 113(2): 887-891, Aug. 24, 2005.

Yang et al., "Microfluidic assisted synthesis of multi-functional polycaprolactone microcapsules: incorporation of CdTe quantum dots, $Fe_3O_4$ superparamagnetic nanoparticles and tamoxifen anticancer drugs," *Lab Chip*, No. 7, pp. 961-965, Dec. 19, 2008.

Yang, "New blood analysis chip could lead to disease diagnosis in minutes," https://phys.org/news/2011-03-blood-analysis-chip-disease-diagnosis.html, Mar. 17, 2011.

Ye et al., "DNA separation with low-viscosity sieving matrix on microfabricated polycarbonate microfluidic chips," *Anal. Bioanal. Chem.*, 381(4): 820-827, Jan. 19, 2005.

Yeo et al., "Ultrafast microfluidics using surface acoustic waves," *Biomicrofluidics*, 3(1): 012002-1-012002-23, Jan. 2, 2009.

Ying et al., "Starch/Polycaprolactone Blends Compatibilized with Starch Modified Polyurethane," *Chem. Res. Chinese Universities*, 26(3): 483-487, 2010.

Yokoyama et al., "Detection and Evaluation of Fragrances by Human Reactions Using a Chemical Sensor Based on Adsorbate Detection," *Anal. Chem.*, 65(6): 673-677, Mar. 15, 1993.

Zhang et al., "A paper-based platform for detection of viral RNA," *Analyst.*, 142(5): 815-823, Feb. 27, 2017.

Zhao et al., "Facile preparation of fluorescence-encoded microspheres based on microfluidic system," *Journal of Colloid and Interface Science*, 352(2): 337-342, Dec. 15, 2010.

Zheng et al., "An amperometric biosensor based on hemoglobin immobilized in poly($\epsilon$-caprolactone) film and its application," *Biosensors and Bioelectronics*, vol. 23, pp. 1562-1566, Jan. 12, 2008.

Zhou et al., "Poly($\epsilon$-caprolactone) as substrate for water denitrification," *Int. J. Environment and Pollution*, 38(3): 349-359, 2009.

Zhu et al., "Surface Modification of Polycaprolactone Membrane via Aminolysis and Biomacromolecule Immobilization for Promoting Cytocompatibility of Human Endothelial Cells," *Biomacromolecules*, 3(6): 1312-1319, Sep. 18, 2002.

Lewis et al., "Quantifying analytes in paper-based microfluidic devices without using external electronic readers," *Angewandte Chemie Int. Ed.*, 51(51): 12707-12710, Nov. 9, 2012.

(56) References Cited

OTHER PUBLICATIONS

Zhang et al., "Naked-eye quantitative aptamer-based assay on paper device," *Biosensors and bioelectronics*, vol. 78, pp. 538-545, Dec. 4, 2015.

\* cited by examiner

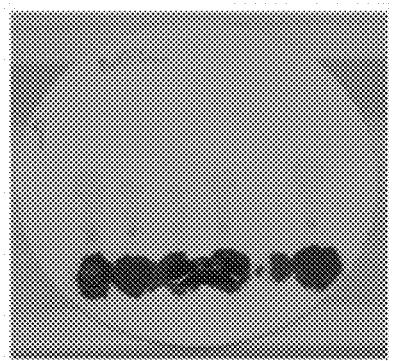
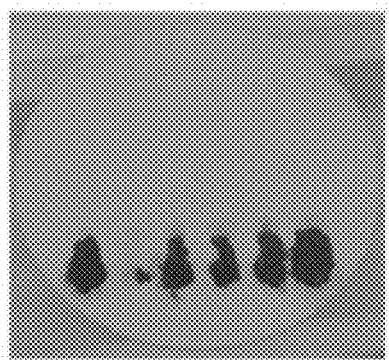
FIG. 14A    FIG. 14B
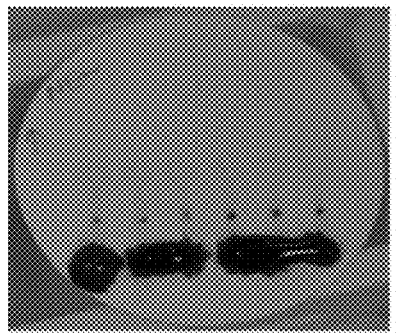
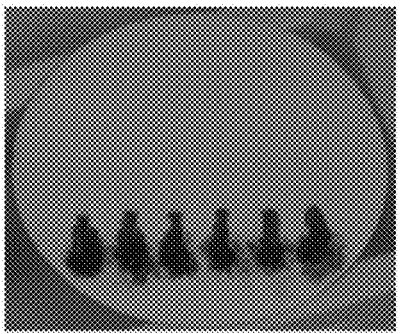
FIG. 15A    FIG. 15B
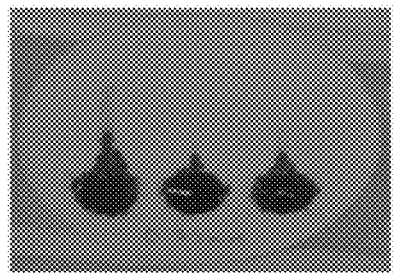
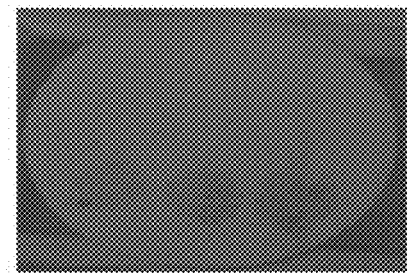
FIG. 16A    FIG. 16B
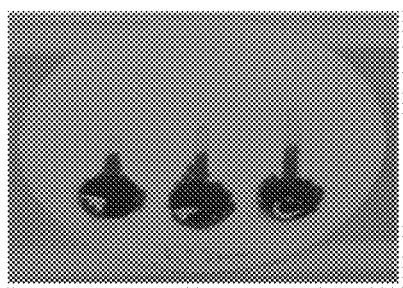
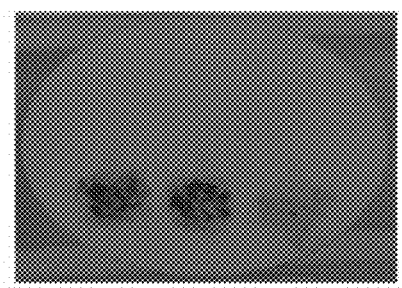
FIG. 17A    FIG. 17B

MEMBRANE DEVICE FOR BLOOD SEPARATION AND METHODS OF MAKING AND USING THE SAME

CROSS REFERENCE TO RELATED APPLICATION

This application is a continuation-in-part of U.S. application Ser. No. 16/410,637 filed on May 13, 2019, which claims the benefit of and priority to the earlier filing date of U.S. Provisional Patent Application No. 62/671,281, filed on May 14, 2018; the present application also claims the benefit of and priority to the earlier filing dates of U.S. Provisional Patent Application No. 62/847,064, filed May 13, 2019, and U.S. Provisional Patent Application No. 62/849,636, filed on May 17, 2019; all of these earlier applications are incorporated by reference herein in their entirety.

FIELD

Disclosed herein are embodiments of a membrane device for blood separation and methods of making and using the same.

BACKGROUND

Blood tests can reveal valuable information about the cause of a disease and its symptoms, enabling early identification of critical health changes before they become severe medical conditions (heart disease, cancer, diabetes, etc.). Blood analysis often involves analyzing different components in a patient's blood sample. Separating blood plasma and/or serum from whole blood allows one to obtain accurate test results, especially when analyzing blood plasma constituents where the cellular fraction can interfere with the analysis. Effectively separating blood plasma is a challenging process that is rarely done in microfluidic platforms and is one of the main challenges that scientists face when developing simple, inexpensive and portable point of care diagnostic tests. There exists a need in the art for new devices that allow quick and accurate blood analysis without having to use complex analytical devices and/or reagents.

SUMMARY

Disclosed herein are embodiments of a membrane device, comprising: a membrane having a first surface and a second surface; a wicking region formed on the membrane, comprising a sample introduction region on the first surface of the membrane; a flow-through via that is directly and fluidly coupled to the sample introduction region and that directs fluid flow from the first surface of the membrane device to the second surface of the membrane; and a fluidic channel that is fluidly and proximally coupled to the flow-through via, wherein the fluidic channel is configured to direct fluid flow in a direction substantially perpendicular to a direction of fluid flow through the flow-through via; wherein the sample introduction region, the flow-through via, and the fluidic channel of the wicking portion are hydrophilic and are structurally defined by a first hydrophobic polymer. In some embodiments, the membrane device can further comprise a capillary flow region, comprising a capillary channel and a sample collection region, wherein the capillary channel is fluidly coupled to the sample collection region and further is fluidly coupled to the fluidic channel of the wicking region; wherein the capillary channel and the sample collection region are structurally defined by a second hydrophobic polymer having a concentration higher than the first hydrophobic polymer. In some embodiments, the membrane can comprise a plurality of any one or more of these structural features. In yet additional embodiments, the membrane can further comprise an assay region, an analyte capture region, electrodes, a volume enhancement region, or any combinations thereof.

Also disclosed herein are embodiments of a method for using the membrane devices for separating blood plasma and/or blood serum from a blood sample. Also disclosed are methods wherein analytes present in a blood sample can be detected. Such methods can comprise depositing a blood sample on the sample introduction region of the membrane; and analyzing a fluidic channel of the membrane, an analyte capture region of the membrane, an assay region of the membrane, or any combination thereof for the presence of an analyte in blood plasma and/or blood serum separated from the blood sample.

Also disclosed are embodiments of a method for making the membrane devices disclosed herein. In some embodiments, the method can comprise placing a first patterned mask on a first surface of the membrane, placing a second patterned mask on a second surface of the membrane, exposing the membrane to an exposure medium, and removing the one or more masks.

The foregoing and other objects and features of the present disclosure will become more apparent from the following detailed description, which proceeds with reference to the accompanying figures.

BRIEF DESCRIPTION OF THE DRAWINGS

FIG. 14A is an image showing results obtained from using a membrane device to separate a blood sample that has been treated with an anticoagulant, wherein the first (or top) surface of the membrane device is shown.

FIG. 14B is an image showing results obtained from using a membrane device to separate a blood sample that has been treated with an anticoagulant, wherein the second (or bottom) surface of the membrane device is shown.

FIG. 15A is an image showing results obtained from using a membrane device to separate a blood sample that has been not treated with an anticoagulant, wherein the first (or top) surface of the membrane device is shown.

FIG. 15B is an image showing results obtained from using a membrane device to separate a blood sample that has not been treated with an anticoagulant, wherein the second (or bottom) surface of the membrane device is shown.

FIG. 16A is an image showing results obtained from using a membrane device having 0.75 mm wide fluidic channels formed at a first (or top) surface of the membrane to separate blood plasma from whole blood, wherein the first surface of the membrane device is shown.

FIG. 16B is an image of a second (or bottom) surface of the membrane device illustrated in FIG. 16A.

FIG. 17A is an image showing results obtained from using a membrane device having 1.25 mm wide fluidic channels formed at a first (or top) surface of the membrane to separate blood plasma from whole blood, wherein the first surface of the membrane device is shown.

FIG. 17B is an image of a second (or bottom) surface of the membrane device illustrated in FIG. 17A.

DETAILED DESCRIPTION

I. Overview of Terms

Figure 1:
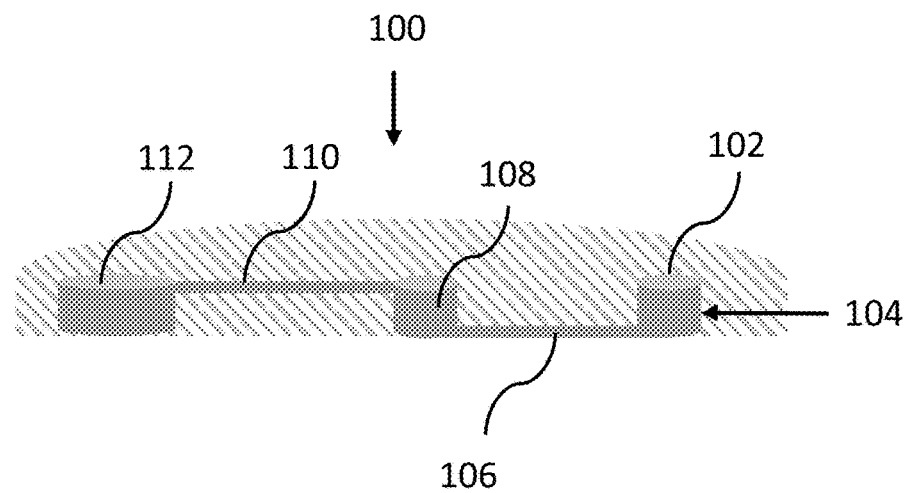
FIG. 1 is a cross-sectional view of a representative membrane device embodiment.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and compounds similar or equivalent to those described herein can be used in the practice or testing of the present disclosure, suitable methods and compounds are described below. The compounds, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well.

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkenyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkynyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, heteroaliphatic, aromatic, other functional groups, or any combination thereof.

Biomolecule: Any molecule that may be included in a biological system, including but not limited to, a synthetic or naturally occurring protein, glycoprotein, lipoprotein, amino acid, nucleoside, nucleotide, nucleic acid, oligonucleotide, DNA, RNA, carbohydrate, sugar, lipid, fatty acid, hapten, and the like.

Capillary Channel: A channel formed in a capillary flow region of a membrane device and that typically has smaller dimensions than a fluidic channel provided in any wicking region that is formed on the same membrane device.

Capillary Flow Region: A region formed on a membrane wherein the region is provided by layering a second polymer layer on top of a layer of a first polymer, wherein the second polymer is more viscous than the first polymer and thereby provides a thicker layer than that provided by the first polymer. In some embodiments, a capillary flow region comprises at least one capillary channel that typically has smaller dimensions than a fluidic channel provided by any wicking region of the membrane device.

Cellulosic Polymer: A polymer made of cellulose or a derivative thereof.

Chemiluminescence: The emission of visible radiation due to a chemical reaction. During the reaction, an excited intermediate is formed. The intermediate subsequently decays to a lower energy level with emission of visible radiation. The reaction may also be accompanied by limited emission of heat.

Elastomeric Polymer: A flexible polymer. Exemplary elastomeric polymers include, but are not limited to, unsaturated rubbers, such as polyisoprene or polybutadiene, and saturated rubbers, such as epichlorohydrin and ethylene-vinyl acetate.

Flow-Through Via: A region in a membrane device that has modified surface chemistry produced by oxygen radical exposure that extends from a first surface of the membrane to a second surface of the membrane and thus is capable of delivering components of samples disclosed herein (e.g., blood, blood serum, and/or blood plasma) from one surface of a membrane to a different surface of the membrane and that is fluidly coupled to one or more fluidic channels that deliver blood serum along a direction that is perpendicular (or substantially perpendicular) to the flow-through via.

Fluidic Channel: A fabricated pathway created on a membrane through which blood plasma and/or blood serum can flow with or without any external forces. In some embodiments, the fluidic channels of membrane devices described herein can be microchannels and/or nanochannels. The term "microchannels," as used herein, is understood to refer to channels having channel width dimensions less than 1 mm and greater than or equal to 1 μm. The term "nanochannels," as used herein, is understood to refer to channels having width dimensions less than 1 μm and greater than or equal to 1 nm. In some embodiments, the fluidic channels of the disclosed devices can have width dimensions greater than 1 mm.

Fluorescence: The emission of visible radiation by an atom or molecule passing from a higher to a lower electronic state, wherein the time interval between absorption and emission of energy is $10^{-8}$ to $10^{-3}$ second. Fluorescence occurs when the atom or molecule absorbs energy from an excitation source (e.g., an ultraviolet lamp) and then emits the energy as visible radiation.

Haloaliphatic: An aliphatic group wherein one or more hydrogen atoms, such as one to 10 hydrogen atoms, independently is replaced with a halogen atom, such as fluoro, bromo, chloro, or iodo.

Haloalkyl: An alkyl group wherein one or more hydrogen atoms, such as one to 10 hydrogen atoms, independently is replaced with a halogen atom, such as fluoro, bromo, chloro, or iodo. In an independent embodiment, haloalkyl can be a $CX_3$ group, wherein each X independently can be selected from fluoro, bromo, chloro, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, silicon, sulfur, selenium, phosphorous, boron, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group.

Membrane: A substrate that is made of a porous or fibrous material and that may be modified to comprise a polymer component. The term "membrane" as used herein does not include non-porous substrates that are made of a core material comprising thermoplastic polymers or thermoset polymers, such as substrates used in "lab-on-a-chip" analysis. In independent embodiments, membranes contemplated by the present disclosure do not include paper substrates without a polymeric coating.

Opening: An aperture or gap in the surface of a substrate or a membrane that allows blood, blood plasma, and/or blood serum to pass through the substrate and/or that serves to contain a blood sample within a perimeter defined by the opening. In some embodiments, openings are surrounded by a hydrophobic polymer component and thus the hydrophobic polymer defines the outer perimeter of the opening.

Sample Introduction Region: A region of a membrane device upon which a blood sample is deposited and that is directly and fluidly coupled to a flow-through via.

Sample Collection Region: A region of a membrane device having a perimeter defined by a first polymer, a second polymer, or a combination thereof and which can contain a sample after it has passed through a fluidic channel, a capillary channel, or a combination thereof. In some embodiments, a sample can be extracted from a device by removing fluid that collects in the sample collection region. In some embodiments, the sample collection region is located in a capillary flow region of a membrane device.

Sump: A region of a substrate used in devices described herein wherein the region is hydrophilic and thus capable of absorbing blood plasma and/or blood serum and serving as a reservoir to help facilitate wicking of a blood plasma and/or blood serum through one or more structural features of membrane device embodiments disclosed herein.

Thermoplastic Polymer: A type of polymer that becomes moldable and malleable above a particular temperature, and that solidifies upon cooling. Exemplary thermoplastic polymers include, but are not limited to, polyamides, polylactic acid, polycarbonate, polyetherimide, polypropylene, polystyrene, polyvinyl chloride, polytetrafluoroethylene, and the like.

Thermoset Polymer: A type of polymer that changes from a soft or viscous state into a hard polymer by curing and does not change shape after curing. Exemplary thermoset polymers include, but are not limited to, polyester resin, polyurethanes, epoxy resin, cyanate esters, and the like.

II. Introduction

Effective separation of blood plasma and/or blood serum is a challenging process that is rarely done in microfluidic platforms and is one of the main challenges that scientists face when developing simple, inexpensive and portable point of care diagnostic tests. Conventional methods of separating plasma/serum from whole blood typically require centrifugation and sample preparation (dilution, addition of standards or reagents, etc.), and usually require trained personnel to conduct the analysis. This makes blood analysis expensive and unacceptable for deployment in resource-limited settings.

Some less-complex devices for blood analysis have been developed in the past few years, such as chip-based devices and/or paper-based devices; however, these devices still require using additional components to facilitate their use (e.g., external pumps to force blood and/or blood plasma flow) and/or fabrication restrictions (e.g., production of three-dimensional structures by stacking multiple paper substrates), which make these devices impracticable for point of care diagnostics and/or that require higher production costs.

The present disclosure, however, describes novel, inexpensive, portable membrane device embodiments that can efficiently separate blood plasma and/or blood serum from whole blood and/or or that can facilitate sample collection after the sample has been passed through the device to thereby provide the ability to conduct further analysis on the sample. The fluidic membrane device embodiments described herein provide a novel and inexpensive fluidic platform that can be used to analyze blood samples in any type of setting (e.g., in the field or in a laboratory). The fluidic membrane device embodiments provide flow-based separation of blood plasma and/or blood serum from whole blood (including unadulterated samples and/or samples that have been treated, such as with an anti-coagulant) using a unique membrane component that has been fabricated to comprise structural features that promote blood flow and separation of blood plasma and/or blood serum from whole blood. The disclosed membrane device embodiments comprise a flow-through via and fluidly-coupled fluidic channel(s) that facilitate blood flow and separation. The disclosed membrane device embodiments can be integrated as a front-end for many chemistries and assays to yield inexpensive point of care diagnostic devices for analyzing different blood plasma and/or blood serum constituents.

Also disclosed herein are novel, unique channel fabrication methods that enable making membrane device embodiments comprising a combination of different channel geometries, which can provide highly accurate and sensitive device performance. The disclosed methods minimize environmental impact as little to no toxic chemicals are required and little to no toxic by-products are produced. The methods also maximize biocompatibility as the constructed fluidic membrane device embodiments can be modified to include a variety of assay components that allow the user to analyze blood samples for myriad analytes (e.g., proteins, toxins, hormones, clotting factors, etc.). In some embodiments, the disclosed methods of making the membrane device embodiments make it possible to integrate specific and/or non-specific assays to independently detect multiple analytes without any additional chemistry or other instrumental/analytical requirements. The methods disclosed herein also provide the flexibility to define the fluidic channel's shape, placement, and dimensions independently. In some embodiments, the shape and dimensions of the fluidic channel can be controlled using a masking technique that does not require expensive fabrication instrumentation and that also provides the ability to mask different surfaces of the substrate of the membrane device.

The membrane device embodiments, methods of making the membrane device embodiments, and methods of using the membrane device embodiments are described in more detail below.

III. Membrane Device Embodiments

Disclosed herein are embodiments of a membrane device that can be used for blood analysis. The membrane device separates blood plasma and/or blood serum from whole blood and/or treated blood (e.g., blood that has been treated with an anti-coagulant). The disclosed membrane device embodiments comprise a membrane that is configured to comprise structural features, such as a sample introduction region, a fluidic channel, and a flow-through via, that facilitate flow of blood plasma and/or blood serum away from an initial whole blood sample. The membrane device also may comprise a plurality of such structural features and/or additional components, which are described in more detail below. In independent embodiments, the membrane device is free of, or does not include, a polymer inclusion membrane or a polymer inclusion membrane spot, such as the polymer inclusion membrane or polymer inclusion membrane spots described by WO 2017/210199. In some embodiments, the membrane device can comprise further structural features that facilitate analysis, fluid gating, and/or collection of a sample after it has passed through the membrane device.

The membrane of the membrane device can be a porous, hydrophilic membrane or a porous, hydrophobic membrane, or a combination thereof. In particular disclosed embodiments, the porous membranes have sufficient porosity so as to allow penetration of oxygen radicals into the membrane to activate the inner surfaces of the membrane. In some embodiments comprising certain hydrophobic membranes, the membrane need not be further modified with a polymeric coating as described herein for other types of membranes, therefore the polymeric coating can be optional. Some hydrophobic membranes (e.g., membranes comprising Teflon) can be coated with a polymeric coating in some embodiments. Hydrophobic membranes can be treated to have hydrophilic regions using methods described herein. The membrane device also is chemically inert and stable and is resistant to heat. In particular disclosed embodiments, the membrane can be a glass microfiber membrane (Whatman GF/A, GF/B, or other substrates), a polymeric membrane (e.g., such as formed from a thin polymer film having a melting point higher than that of the polymer used to coat or substantially coat the membrane), a nylon-based membrane, or a combination thereof. The membrane device embodiments can have any shape, such as circular, ellipsoidal, square, rectangular, and other geometric shapes. In some embodiments, the membrane can have a thickness ranging from 115 μm to 730 μm, such as 260 μm to 600 μm, or 260 μm to 675 μm or 115 μm to 420 μm. In particular embodiments, the membrane can be a glass microfiber substrate having a thickness ranging from 260 μm to 730 μm, such as 260 μm to 675 μm with particular embodiments having a thickness of 260 μm. In some independent embodiments, the membrane can be a filter or chromatography paper having a thickness ranging from 115 μm to 420 μm. In some embodiments, the surfaces of the membrane (e.g., a first surface, such as a top surface; and a second surface, such as a bottom surface) can be coated or substantially coated with a polymer, which is described herein. In some embodiments, the membrane device can comprise a plurality of membrane devices that are fluidly coupled in series (either vertically or horizontally), in parallel, or a combination thereof.

In yet some additional embodiments, surfaces of the membrane can be coated or substantially coated with a first polymer and can further be modified such that a portion of the membrane is coated with a second polymer that is has a different chemical identity from the first polymer, or that has a different concentration than the first polymeric, or both. Such membrane embodiments provide dual wicking and fluid collection capabilities. In particular embodiments, the second polymer is applied at a higher concentration than the first polymer and thus forms a thicker and/or harder coating on the region to which it is applied. In such embodiments, a region of the membrane comprising the first polymer provides a wicking region and the region of the membrane comprising the second polymer provides a capillary flow region. Features and properties of these types of regions are discussed in more detail herein.

In some embodiments, the polymer used on the membrane device is a polymer having a structure satisfying Formula I, below. In some embodiments, this polymer can be used as the first and/or second polymer material in membrane embodiments configured to provide dual wicking and collection capabilities.

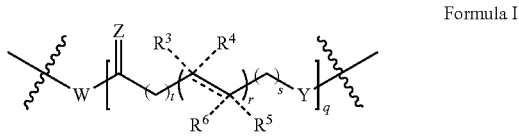

Formula I

With reference to Formula I, Z, Y, and W independently may be selected from O, S, NH, and $NR^2$, where $R^2$ may be selected from hydrogen, aliphatic, aryl, and heteroaryl; each of $R^3$, $R^4$, $R^5$, and $R^6$ (if present) independently may be selected from hydrogen, aliphatic, aryl, heteroaryl, and a heteroatom-containing moiety selected from halogen (e.g. F, Cl, Br, and I), aldehyde (—$R^a$CHO), acyl halide (—$R^a$C(O)X) (where X is selected from fluorine, chlorine, bromine, and iodine), carbonate (—$R^a$OC(O)$OR^b$), carboxyl (—$R^a$C(O)OH), carboxylate (—$R^a$COO—), ether (—$R^a$$OR^b$), ester (—$R^a$C(O)$OR^b$, or —$R^a$OC(O)$R^b$), hydroxyl (—$R^a$OH), ketone (—$R^a$C(O)$R^b$), silyl ether ($R^bR^cR^d$SiO$R^a$—), peroxy (—$R^a$OO$R^b$), hydroperoxy (—$R^a$OOH), phosphate (—$R^a$OP(O)(OH)$_2$), phosphoryl (—$R^a$P(O)(OH)$_2$), phosphine (—P$R^aR^bR^c$), thiol (—$R^a$SH), thioether/sulfide (—$R^a$SR), disulfide (—$R^a$SS$R^b$), sulfinyl (—$R^a$S(O)$R^b$), sulfonyl (—$R^a$SO$_2R^b$), carbonothioyl (—$R^a$C(S)$R^b$ or —$R^a$C(S)H), sulfino (—$R^a$S(O)OH), sulfo (—$R^a$SO$_3$H), thiocyanate (—$R^a$SCN), isothiocyanate (—$R^a$NCS), oxazole, oxadiazole, imidazole, triazole, tetrazole, amide (—$R^a$C(O)N$R^bR^c$, or —$R^a$N$R^b$C(O)$R^c$), azide (N$_3$), azo (—$R^a$NN$R^b$), cyano (—$R^a$OCN), isocyanate (—$R^a$NCO), imide (—$R^a$C(O)N$R^b$C(O)$R^c$), nitrile (—$R^a$CN), isonitrile (—$R^a$N$^+$C$^-$), nitro (—$R^a$NO$_2$), nitroso (—$R^a$NO), nitromethyl (—$R^a$CH$_2$NO$_2$), and amine (—$R^a$NH$_2$, —$R^a$NH$R^b$, —$R^a$N$R^bR^c$), wherein $R^a$ can be selected from a bond, aliphatic, aryl, heteroaliphatic, or heteroaryl; and each $R^b$, $R^c$, and $R^d$ independently is selected from hydrogen, aliphatic, aryl, heteroaliphatic, heteroaryl, and any combination thereof. In particular disclosed embodiments, Formula I may comprise one or more conjugated or unconjugated olefins. In embodiments where Formula I comprises one or more conjugated or unconjugated olefins, only one of $R^3$ and $R^4$ and only one of $R^5$ and $R^6$ is present in Formula I. In embodiments where Formula I does not comprise one or more conjugated or unconjugated olefins, all of $R^3$, $R^4$, $R^5$, and $R^6$ may be present in Formula I. In particular disclosed embodiments, r may range from 1 to 4, more typically from 1 to 3; even more typically from 1 or 2; s and t independently may range from 0 to about 4 or 0 to 3, or 0 to 2, or 0 to 1;

more typically s and t range from 1 to 4, or 1 to 3, or 1 to 2. In particular disclosed embodiments, q ranges from at least 1 to about 1000, or at least 1 to about 900, or at least 1 to about 800, or at least 1 to about 700, or at least 1 to about 600, or at least 1 to about 500, or at least 1 to about 300, or at least 1 to about 250, or at least 1 to about 200, or at least 1 to about 150, or at least 1 to about 100.

In particular disclosed embodiments, the polymer has a Formula II, III, or IV, each of which is illustrated below. Each of W, Z, Y, $R^3$, $R^4$, $R^5$, $R^6$, q, and r can be as recited above. Such polymer embodiments also can be used as the first and/or second polymer in membrane device embodiments configured to provide dual wicking and collection capabilities.

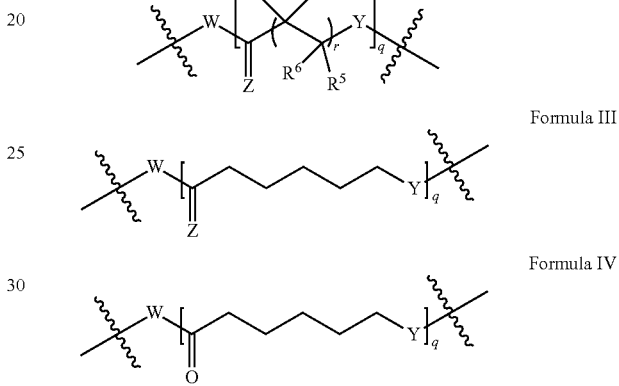

In particular embodiments, the polymer may be selected from the following exemplary compounds: polycaprolactone, polycaprolactone diol, polycaprolactone triol, polycaprolactone-block-polytetrahydrofuran-block polycaprolactone, poly(ethylene oxide)-block-polycaprolactone, poly(ethylene glycol)-block-poly(e-caprolactone) methyl ether, and combinations thereof. In particular disclosed embodiments, the polymer can be any other suitable polymer having ester or epoxy groups, such as polylactic acid, polyvinyl chloride, or polyvinyl acetate, or an epoxy-based polymer, such as SU-8. In some embodiments, these polymers can be used as the first and/or second polymer material in membrane device embodiments configured to provide dual wicking and collection capabilities.

Particular disclosed working embodiments concern using polycaprolactone as a polymer, the structure for which is shown below (wherein q is as recited herein). In particular disclosed embodiments, the polycaprolactone has a molecular weight ranging from 500 g/mol to 100,000 g/mol (or higher); more typically from 10,000 g/mol to 80,000 g/mol, or 20,000 g/mol to 50,000 g/mol, or 10,000 g/mol to 14,000 g/mol; more typically from 70,000 g/mol to 90,000 g/mol. Any polycaprolactone compounds or derivatives thereof having any molecular weight falling within the disclosed ranges are contemplated by the present disclosure. In exemplary embodiments, the polymer is polycaprolactone having a molecular weight of 25,000 g/mol. In some embodiments, this polymer can be used as the first and/or second polymer material in membrane device embodiments configured to provide dual wicking and collection capabilities.

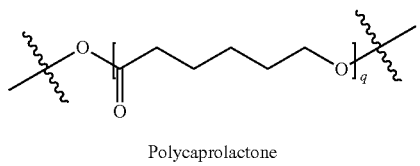

Polycaprolactone

The polymer typically is used to coat the membrane of the membrane device as described herein. In particular disclosed embodiments, a coating of the polymer can have a thickness ranging from 0.01 μm to 5 μm or may consist of an embedded (permeating) format. In such embedded/permeating embodiments, an amount of the polymer can be added to the membrane by way of a solution such that it partially permeates or completely saturates the membrane. In such embodiments, the solution of the polymer can comprise the polymer in an amount ranging from greater than 0% w/v to 75% w/v of the polymer, such as 1 to 75% w/v, or 1% w/v to 30% w/v, or 5% w/v to 20% w/v, or 5% w/v to 15% w/v, with particular embodiment using 15% w/v polymer in toluene. In some embodiments, 5 mL to 15 mL of the polymer solution can be added, such as 8 mL to 10 mL or 10 mL. In particular embodiments the polymer is located entirely within the matrix of the membrane from a depth of 0.1% to 100% of the depth of the membrane. In particular disclosed embodiments, the polymeric solution penetrates surfaces of the membrane and coats (or substantially coats) internal fibers or portions of the membrane located between the surfaces. In embodiments where the surfaces and/or internal fibers/portions of the membrane are substantially coated, the polymer covers greater than 0% to less than 100% of the surface area of each substrate surface and/or internal fibers/portions, such as 50% to 99%, or 60% to 98%, or 70% to 97%, or 80% to 95% of the surface area of each surface and/or internal fibers/portions. In yet additional embodiments, a second polymer can also be applied to the membrane such that it coats a region of the membrane, but leaves exposed at least a portion of the membrane comprising a coating of the first polymer. In particular embodiments, the second polymer is chemically identical to the first polymer but is applied at a higher concentration so that a thicker and/or harder coating of the second polymer is provided. In some embodiments, the concentration of the second polymer can be any concentration sufficient to provide a more viscous solution of the second polymer (as compared to the solution comprising the first polymer). Exemplary concentration ranges for the second polymer are disclosed herein. The region of the membrane comprising the second polymer can be used as a capillary flow region through which a blood sample can flow and be collected after having been purified, analyzed, and/or assayed. The region of the membrane comprising the first polymer can be used as a wicking region in which the blood sample can be purified, analyzed, and/or assayed.

The membrane device typically comprises a sample introduction region, a flow-through via, and a fluidic channel. Each of the sample introduction region, the flow-through via, and the fluidic channel is hydrophilic. In some membrane device embodiments comprising both a wicking region and a capillary flow region, the sample introduction region, the flow-through via, and the fluidic channel can be fabricated in the wicking region of the membrane. The hydrophilic nature of these structural features can be inherent in the sense that the membrane is hydrophilic and these structural features comprise exposed/unmodified portions of the membrane, or it can result from treating a non-hydrophilic substrate comprising such structural features with a treatment that renders them hydrophilic. The sample introduction region is a region of a first surface of the membrane that is configured to accept a blood sample and serves as the point of entry of the blood sample into the flow-through via. Typically, the sample introduction region is defined by hydrophobic regions of the membrane. In embodiments where the membrane is a hydrophilic membrane that has been treated to be hydrophobic using a polymer as described above, the sample introduction region is defined by boundaries of the polymer material added to a first surface of the membrane. These boundaries can be formed with masks as described herein. Membrane device embodiments described herein can comprise a single sample introduction region or a plurality of sample introduction regions.

The flow-through via is fluidly coupled to a sample introduction region of the membrane device and typically is directly fluidly coupled such that the sample introduction region is positioned directly adjacent to the flow-through via such that no lateral flow along a membrane surface occurs prior to blood, blood plasma, and/or blood serum flow from the sample introduction region into the flow-through via. That is, blood samples added to the membrane device at the sample introduction region immediately flows from the sample introduction region through the flow-through via. In particular disclosed embodiments, the sample introduction region itself serves as the flow-through via. A fluidic channel can be proximally and fluidly coupled to the flow-through via such that blood plasma and/or blood serum is delivered from the flow-through via into the fluidic channel where it flows in a direction through the fluidic channel that is perpendicular (or substantially perpendicular) to the direction of blood, blood plasma, and/or blood serum flow through the flow-through via. In some embodiments, the membrane device can be fabricated to have a plurality of sample introduction regions, flow-through vias, and fluidly coupled fluidic channels. In some embodiments, the membrane device can comprise a first flow-through via that is fluidly coupled to the sample introduction region and that also is coupled to a plurality of fluidic channels that divert flow in different directions on the membrane. The plurality of fluidic channels can individually be distally and fluidly coupled to an additional flow-through via or they can rejoin together such that blood plasma and/or blood serum flow from all fluidic channels is direct to an additional single flow-through via. The plurality of fluidic channels can be arranged in parallel or in any other desired geometrical arrangement. In particular embodiments, the fluidic channel is formed such that it passes along one or more surfaces of the membrane. The flow-through vias facilitate delivery of blood, blood plasma, and/or blood serum between different surfaces of the membrane so that lateral flow can occur through fluidic channels on a first surface of the membrane and/or through fluidic channels on a second surface of the membrane device. As such, any additional flow-through vias included in the membrane device can be used to redeliver blood plasma and/or blood serum from a second surface of the membrane back to the first surface of the membrane where the blood sample was first introduced via the sample introduction region and its directly coupled flow-through via. The additional flow-through vias can, in some embodiments, be used to deliver blood, blood plasma, and/or blood serum flow between different membrane devices that are fluidly coupled, such as in embodiments where a plurality of membrane devices are fluidly coupled in parallel or in series.

An exemplary membrane device embodiment for blood analysis is illustrated in FIG. 1. Membrane device 100 comprises a sample introduction region 102 that is fluidly coupled to flow-through via 104, which in turn is fluidly coupled to fluidic channel 106. Fluidic channel 106 is proximally and fluidly coupled to flow-through via 104. As shown by FIG. 1, the membrane device can comprise an additional flow-through via 108, wherein fluidic channel 106 is distally and fluidly coupled to the additional flow-through via. An additional fluidic channel 110 can be included that is proximally and fluidly coupled to additional flow-through via 108. The membrane device also can comprise an assay region 112. Assay regions are described in more detail below.

A person of ordinary skill in the art will recognize, with the benefit of the present disclosure, that the dimensions of the flow-through vias and fluidic channels described herein can be modified depending on the amount of sample to be analyzed and/or the rate of flow desired during use. In some embodiments, the dimensions of the flow-through vias are larger than the fluidic channels such that a larger volume of sample can be contained by the flow-through vias than can be contained by the fluidic channels. In embodiments where the membrane device is a microfluidic membrane device, the dimension of the flow-through vias and the fluidic channels are on the micrometer scale. Membrane devices also can be configured to have dimensions that are larger or smaller than micrometer dimensions. In some embodiments, wider channels can accommodate higher concentrations (e.g., greater than 10 µL) of a blood sample and narrower channels can be used to evaluate samples having lower concentrations (e.g., less than 10 µL) of a blood sample. In some embodiments, the fluidic channel can have dimensions as follows: widths ranging from 0.05 mm to 5 cm or higher, such as 0.1 mm to 5 mm, or 0.1 mm to 3 mm, or 0.5 mm to 2 mm, or 0.6 mm to 1.25 mm, or 0.75 mm to 1.25 mm, and lengths ranging from greater than 0 mm to 10 cm or higher, such as 0.05 mm to 10 cm, or 0.5 mm to 100 mm, or 0.5 mm to 50 mm, or 0.5 mm to 25 mm, or 0.5 mm to 5 mm. A person of ordinary skill in the art recognizes that these dimensions can be modified to increase and/or decrease based on the size of the membrane device, so long as sufficient flow through the channel is obtained.

In some embodiments, the membrane device is configured to comprise one or more assay regions. Assay regions of the membrane device typically are coupled to a fluidic channel of the membrane device such that the fluidic channel is distally and fluidly coupled to the assay region; that is, the assay region is positioned away from the sample introduction region such that the fluidic channel is positioned between the sample introduction region and the assay region. This configuration facilitates blood, blood plasma, and/or blood serum flow from the sample introduction region through structural features of the membrane device that are fluidly coupled to the sample introduction region and then to the assay region. This configuration of flow allows separation of blood plasma and/or blood serum from a blood sample introduced on the sample introduction region, as discussed herein. The assay regions can comprise or can be configured to accept an assay platform. In some embodiments the assay region comprises an assay platform that is built into the membrane device. The assay region is thus pretreated with one or more reagents to provide the built-in assay platform. In other embodiments, assay regions are configured to accept separate assay platforms that are added to the membrane device prior to use. In such embodiments, the assay platforms can comprise one or more substrates comprising assay reagents. In some embodiments, the substrate comprises a textured area that is configured to match the shape and dimensions of the assay region to which it is added. The assay platform can comprise any material suitable for accepting assay reagents, which can be provided neat or as a solution. In particular disclosed embodiments, the assay platform is made of a microfiber material, such as a glass microfiber material or a polymer-filled glass microfiber material; a cellulosic material, such as paper, a nitrocellulose membrane; a fine woven material, such as nylon or other polymers; and natural materials, such as cotton or wool. In particular disclosed embodiments, the assay platform comprises a borosilicate glass material. In some embodiments, the particular choice of material can depend on assay conditions, such as reagent composition (e.g., solvent compatibility). Materials also may be selected based on the detection mechanism. For example, with solid opaque materials, the ability to read through the material (such as in UV-VIS instruments, which use a top or bottom read with illumination from the opposite side) is reduced and can thereby decrease the observable signal. This can be avoided by selecting a particular material that improves readability of the signal. In some embodiments using fluorescence detection, illumination and detection occur from the same side and thus one can use a variety of materials so long as the background fluorescence is low enough to not interfere with the assay.

A plurality of assay regions and assay platforms can be included in membrane device embodiments so that different assays can be conducted concurrently. Each assay region and assay platform can be fluidly coupled to different fluidic channels such that blood plasma and/or blood serum can be introduced into a single assay platform by a single fluidic channel. Having separate assay regions and assay platforms facilitates the ability to conduct a complete analysis of a blood sample using the same membrane device and further provides the ability to utilize different detection techniques for one single sample.

The assay platform is configured to comprise one or more reagents that are selected to react with analytes that may be present in the blood sample. Any reagents typically used in blood plasma and/or blood serum analysis can be included in the assay platform, with particular embodiments using reagents that can be used to detect analytes, such as total protein, bilirubin, blood urea nitrogen, cholesterol, triglycerides, creatinine, iron, inorganic phosphorus, homocysteine, glucose, carbon dioxide, calcium, fructosamine, β-hydroxybutyrate, and the like. Assay platforms can be pretreated to include assay components from commercially available assays that are used to detect such analytes.

In some embodiments, the membrane device is configured to further comprise an analyte capture region. Typically, the analyte capture region is positioned within a fluidic channel, but it can be included in other regions of the membrane device that come into contact with blood plasma and/or blood serum from samples. The analyte capture region is a region of the membrane device that is modified to comprise reagents that are capable of binding to analytes present in a sample introduced to the membrane device. The immobilized reagents can be provided by first modifying the surface chemistry of the membrane in a fluidic channel. For example, as the fluidic channel is hydrophilic, it includes surface functional groups that are capable of covalently binding with functional groups of a reagent and/or that can absorb or adsorb a solution comprising the reagent. Solely by way of example, fluidic channels of the membrane can comprise surface chemistries having free hydroxyl groups that can form covalent bonds with a reagent to be immobilized on the analyte capture region, such as biomolecules (e.g., antibodies, antigens, or the like) and/or other types of reagents used immunoassays, such as in competitive binding assays, biochemical sandwich assays, direct binding assays, and the like. In other embodiments, a separate substrate comprising an immobilized reagent can be positioned such that it comes into contact with blood, blood plasma, and/or blood serum flowing through fluidic channels of the membrane device.

The immobilized reagents are able to interact with analytes in the blood plasma and/or blood serum such that they bind the analytes. Suitable detection techniques, such as fluorescence analysis, chemiluminescence analysis, chromogenic analysis, and the like, can be used to determine the presence of the analytes after they have interacted with the immobilized reagent. A plurality of analyte capture regions can be positioned within a single fluidic channel, or individual analyte capture regions can be positioned within individual fluidic channels wherein the membrane device comprises a plurality of fluidic channels. The analyte capture regions can be positioned in fluidic channels located at a first surface of the membrane, or in fluidic channels located at a second surface of the membrane, or both. Embodiments of the membrane device comprising an analyte capture region also can be used for detecting trace analytes present in a blood sample. In some such embodiments, an absorption region is fabricated into the membrane device such that the absorption region is positioned downstream of the sample introduction region. Plasma flow rate through fluidic channels fluidly coupled to the absorption region is much faster than the flow rate of blood cells and thus higher volumes of plasma can be separated from whole blood before the cells flow into the absorption region, which facilitates pre-concentration of trace analytes from blood plasma and/or blood serum at the analyte capture region. The analyte capture region is positioned near the absorption region of the membrane. The absorption region can then serve as a sump to generate the capillary flow required to draw the larger sample volume needed from the sample introduction region. As the plasma flows through the fluidic channel, the analyte capture region interacts with trace analytes present in the plasma and facilitates concentration of the analytes as flow to the absorption region continues.

Figure 2A:
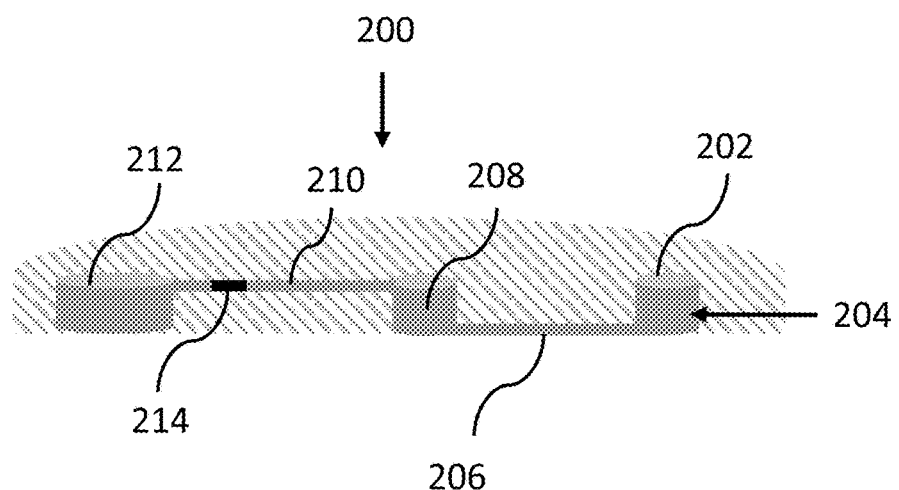
FIG. 2A is a cross-sectional view of a representative membrane device embodiment comprising an analyte capture region.
Figure 2B:
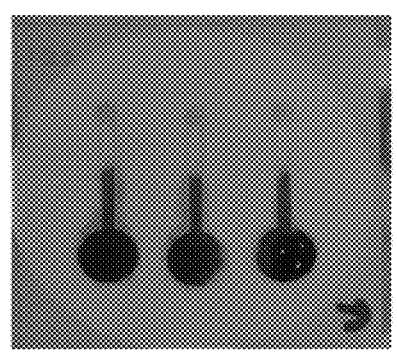
FIG. 2B is an image of a membrane device embodiment showing blood plasma concentrated in an assay region of the membrane away from the whole blood sample added to a sample introduction region.

An exemplary membrane device comprising an analyte capture region is illustrated in FIG. 2A. As illustrated in FIG. 2A, membrane device embodiment 200 can comprise a sample introduction region 202, a directly coupled flow-through via 204, a fluidic channel 206, which in turn is coupled to an additional flow-through via 208, another fluidic channel 210, and an absorption region 212. An analyte capture region 214 is provided on fluidic channel 210 prior to the absorption region 212. FIG. 2B is an image of a representative membrane device wherein blood plasma and/or blood serum has saturated an assay region of a membrane device.

In additional embodiments, the membrane device can comprise a capillary flow region. As discussed herein, the capillary flow region can be provided by coating a region of the membrane with a second polymer that is applied as a higher concentration (more viscous) solution as compared to the solution of the first polymer used to first coat the membrane (and to provide the wicking region). In some embodiments, the second polymer has a concentration ranging from 5% w/v to 70% w/v, such as 10% w/f to 60% w/v, or 20% w/v to 50% w/v, or 20% w/v to 30% w/v. In some embodiments, the second polymer can have a similar molecular weight as the first polymer, embodiments of which are described herein. In some embodiments, the second polymer has a molecular weight of 37,000 Da. The capillary flow region can be configured to comprise one or more capillary channels and one or more sample collection regions. Some or all of the one or more capillary channels are configured to be fluidly coupled to the one or more sample collection regions and also are fluidly coupled to at least one fluidic channel located within a wicking region of the membrane.

The capillary channels of the capillary flow region can be fabricated using a laser cutter or other suitable cutting device to form the capillary channels, wherein the walls defining the capillary channels are provided by the second polymer. In some embodiments, the capillary channels can have widths ranging from 10 µm to 200 µm, such as 20 µm to 200 µm, or 30 µm to 160 µm, or 50 µm to 140 µm. In some embodiments, the capillary channels can have lengths ranging from 0.01 cm to 1 cm (or more), such as 0.2 mm to 8 mm, or 2 mm to 7 mm, or 4 mm to 6 mm. Each capillary channel can have the same or different dimensions as any other capillary channel.

In some embodiments, a plurality of capillary channels can be formed that run in parallel to one another. In such embodiments, each capillary channel of the plurality can be configured to accept fluid flow from a separate flow channel of the wicking region of the membrane, or each capillary channel of the plurality can be configured to accept fluid flow from a single flow channel of the wicking region of the membrane.

Figure 3A:
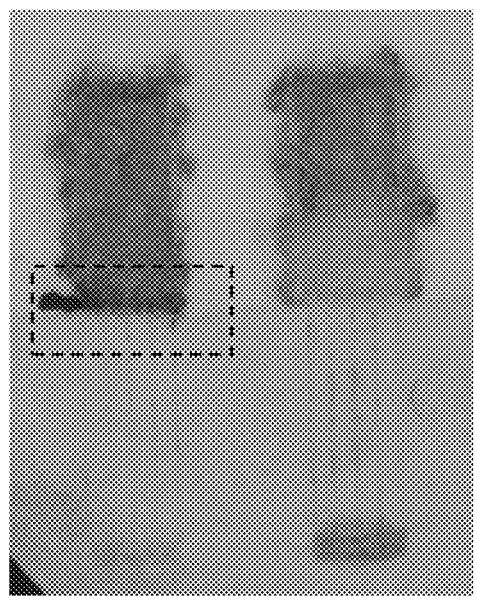
FIG. 3A shows a membrane device embodiment comprising offset features (contained with the region defined by the dotted lines) thereby providing the ability to gate flow through a wicking region and capillary flow region of the membrane device.
Figure 3B:
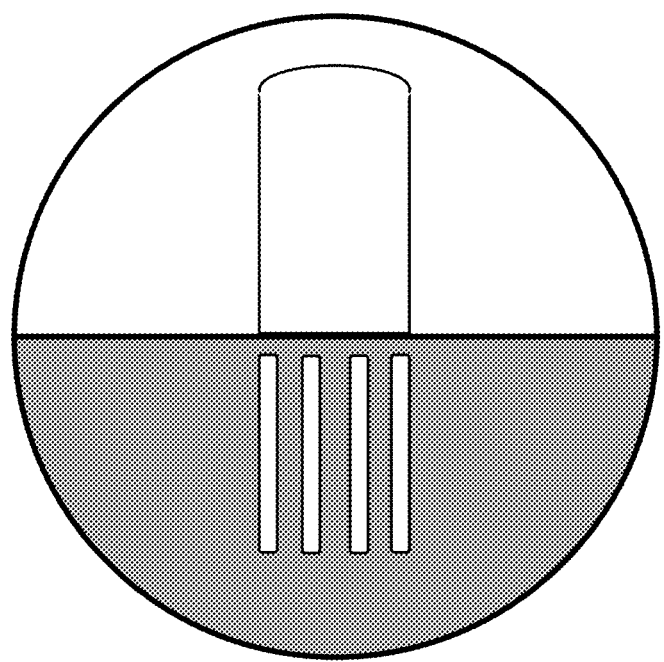
FIG. 3B is an illustration showing the offset nature of the features of the membrane device embodiment shown in FIG. 3A.

In yet additional embodiments, one or more capillary channels can be positioned in the capillary flow region such that they are offset from any fluidic channels of the wicking region. In such embodiments, fluid is able to flow from the capillary flow region to the wicking region via one or more capillary channels of the capillary flow region which can still deliver fluid to the fluidic channels of the wicking region; however, fluid is not able to flow from the wicking region to the capillary flow region due to the offset nature of the capillary channels relative to the fluidic channels. Such embodiments provide gated fluid control. For example, this offset configuration can be used in embodiments where it is desirable to allow separated reactant mixing in one region of the membrane device, but also allow the reactant to mix at a later point in time with a separate sample or buffer fluid. In some embodiments comprising an offset configuration, any sample collection regions in the capillary flow region can also serve as sample introduction regions. An exemplary embodiment comprising offset features is shown in FIGS. 3A and 3B. FIG. 3A shows an exemplary embodiment wherein a region comprising the offset features is shown (contained in the box defined by the dotted line). The offset features are illustrated in FIG. 3B.

Each capillary channel of the plurality also can be configured to deliver fluid to a separate sample collection region of the capillary flow region of the membrane, or each capillary channel of the plurality can be configured to deliver fluid to the same, single sample collection region of the capillary flow region of the membrane. In some embodiments, two or more capillary channels can be present in the capillary flow region. In yet some additional embodiments, a plurality of capillary channel configurations can be present in the capillary flow region, wherein each capillary channel configuration comprises one or more capillary channels, and wherein the capillary channels of each capillary channel configuration can have the same or different dimensions and/or can be present in different numbers. In some embodiments, the number of capillary channels and/or capillary channel configurations can be increased so as to increase the volume of fluid collected in sample collection regions of the capillary flow region.

The sample collection region is a region located in the capillary flow region of a membrane that is defined in the coating provided by the layers of the first polymer, second polymer, or a combination thereof. The sample collection region can be fabricated using a laser cutter or other technique sufficient to form a well within the layer(s) of the second polymer and/or first polymer that are formed on the membrane. The sample collection regions allow for fluid accumulation such that the fluid can be collected and separated from the membrane device. In some embodiments, blood that is collected within a sample collection region can be extracted with a pipette or other extraction tool and then can be analyzed with analytical devices separate from the membrane device. The diameter of each sample collection region can be modified so as to facilitate higher or lower volumes of fluid collection.

Figure 4A:
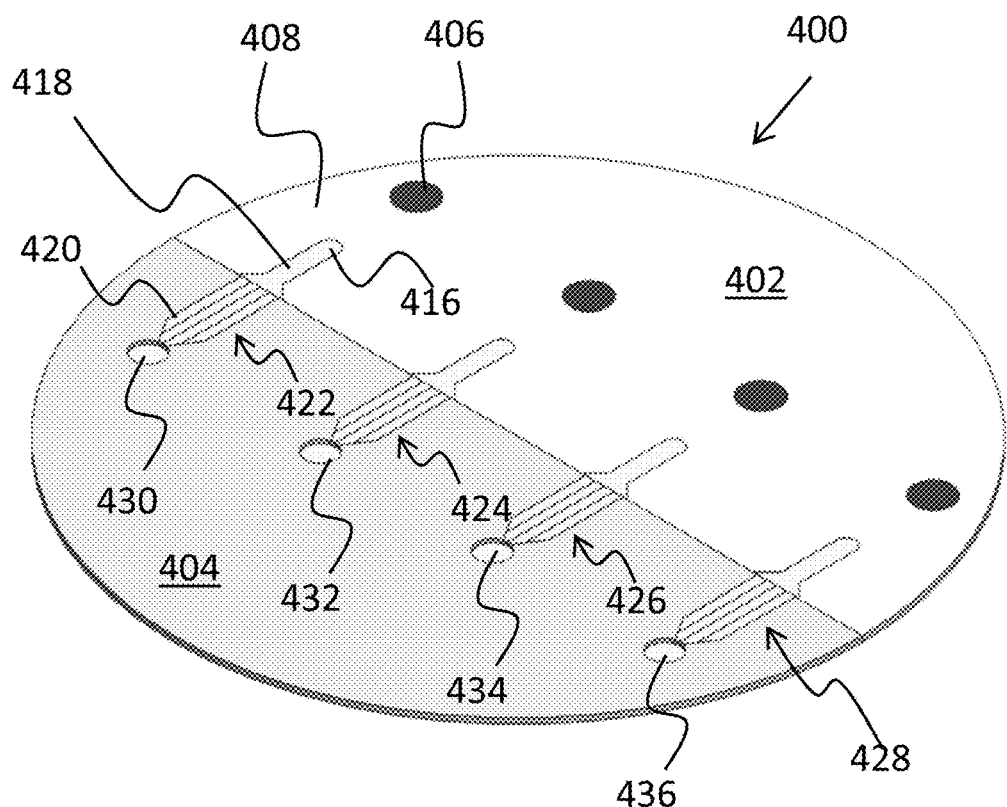
FIG. 4A illustrates a representative device embodiment comprising a wicking region and corresponding features and a capillary flow region comprising capillary channels and sample collection regions, wherein features found on a first surface of the device embodiment are shown.
Figure 4B:
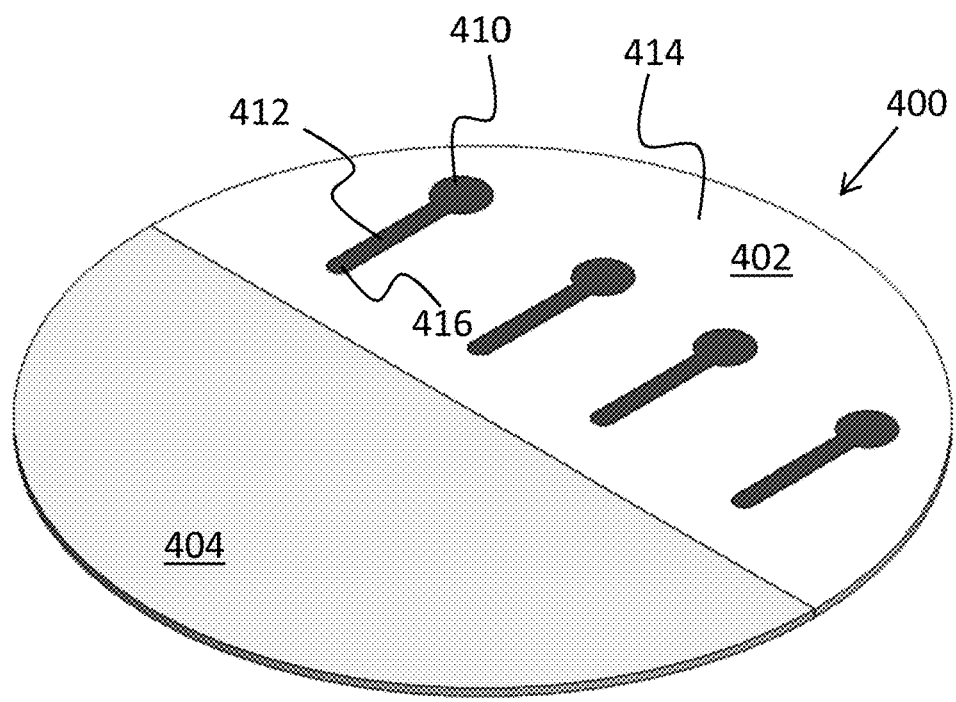
FIG. 4B illustrates a second surface of the representative device embodiment illustrated in FIG. 4A.

An exemplary embodiment of a membrane device comprising a wicking region and a capillary flow region is illustrated in FIGS. 4A and 4B. FIG. 4A illustrates features of a first surface of the membrane device and FIG. 4B shows a second surface of the membrane device. With reference to FIG. 4A, membrane device 400 comprises wicking region 402 and capillary flow region 404. Wicking region 402 further comprises a sample introduction region 406 located on a first surface 408 of the membrane, which is fluidly coupled to a first flow-through via 410 (illustrated in FIG. 4B), which in turn is fluidly coupled to fluidic channel 412 that flows along second surface 414 of the membrane (FIG. 4B). The fluid is then redirected to first surface 408 through a second flow-through via 416 and into fluidic channel 418 located on the first surface. As shown in FIG. 4A, fluidic channel 418 is fluidly coupled to capillary channels 420, which are formed in capillary flow region 404. The embodiment shown in FIG. 4A comprises a plurality of capillary channel configurations, such as capillary channel configurations 422, 424, 426, and 428. Each capillary channel configuration can comprise a plurality of capillary channels positioned parallel to one another. The capillary channels can be fluidly coupled to one or more sample collection regions, such as sample collection regions 430, 432, 434, and 436. As fluid, such as a blood sample, passes through channels of the membrane device, it will collect in the sample collection regions and can then be extracted from the device.

Membrane device embodiments described herein also can comprise electrodes to facilitate electrochemical detection techniques. In some embodiments, one or more electrodes can be coupled to a fluidic channel or an assay region of the membrane device such that the fluidic channel is distally and fluidly coupled to the electrode, or they can be positioned externally to the membrane device but in close proximity to the fluidic channel and/or assay regions such that the electrode can become wetted by the fluid flowing through the fluidic channel and/or the fluid contained within the assay region. In such embodiments, the electrode is positioned downstream of the sample introduction region so that as the blood plasma and/or blood serum flows through the flow-through vias and/or fluidic channels it will eventually pass over the electrode. In some embodiments, one or more electrodes are positioned in the assay region of a membrane device. The electrode is coupled to a potentiometer and a potentiostat with one or more potentiometer and/or potentiostat connections that are electrically coupled to the electrode. A working electrode and a reference electrode can be included to facilitate electrochemical detection.

Figure 5:
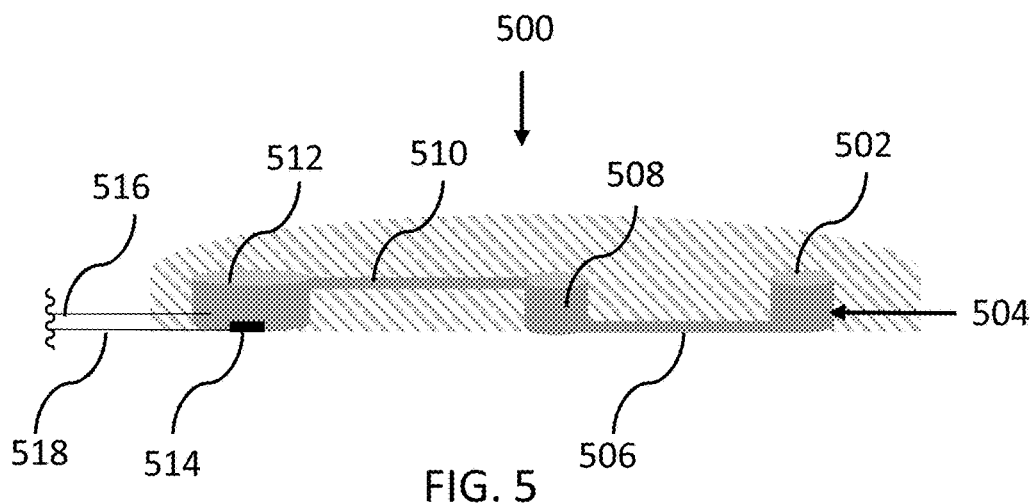
FIG. 5 is a cross-sectional view of a representative membrane device embodiment comprising electrodes in an assay region for electrochemical detection.

An exemplary membrane device comprising electrodes is illustrated in FIG. 5. As illustrated in FIG. 5, membrane device embodiment 500 can comprise a sample introduction region 502, a directly coupled flow-through via 504, a fluidic channel 506, which in turn is coupled to an additional flow-through via 508, another fluidic channel 510, and an assay region 512. Assay region 512 is modified to include an electrode 514, which can be electrically coupled to a potentiometer and potentiostat through connection 518, and a reference electrode.

Figure 6:
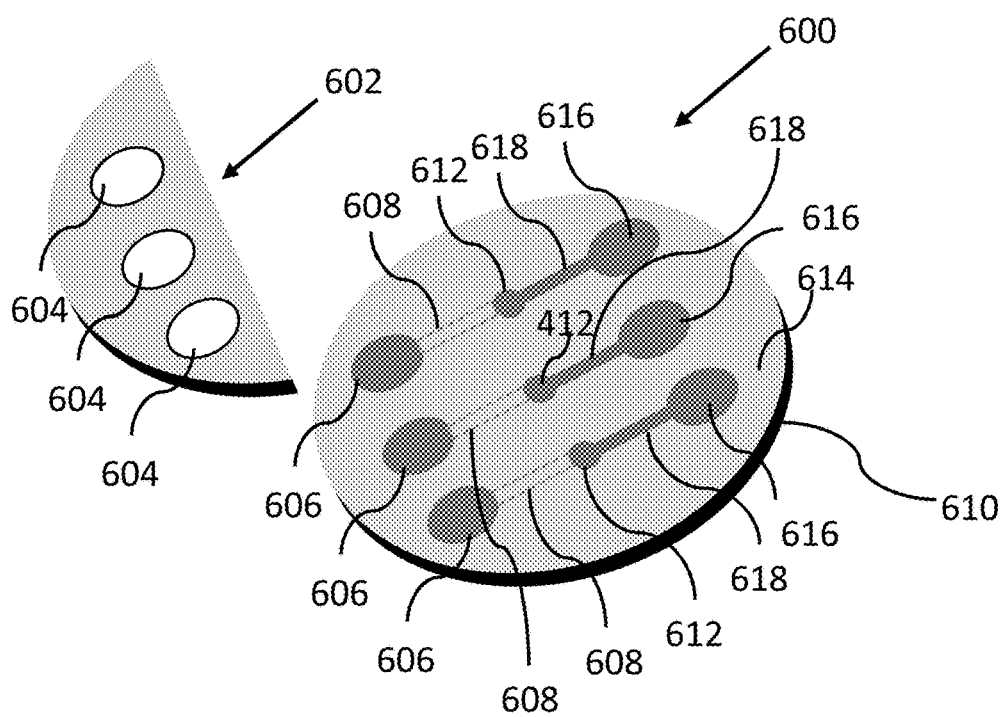
FIG. 6 is an exploded, top plan view of a membrane device embodiment comprising a volume enhancement region 602 that becomes associated with membrane device 600.
Figures 7A, 7B:
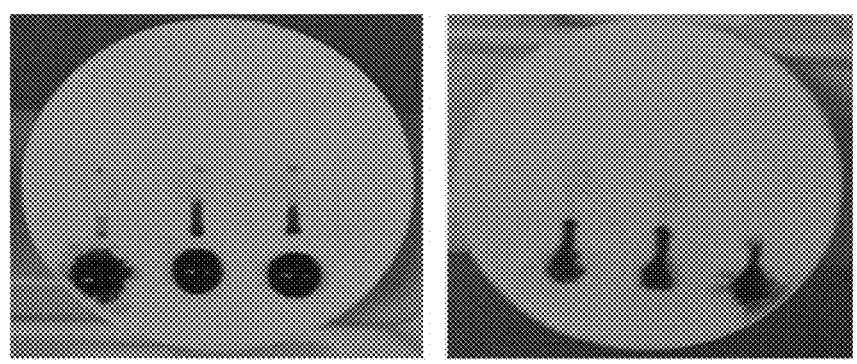
FIG. 7A is an image of a first (or top) surface of a membrane device comprising a volume enhancement region for introducing high-volume samples.
FIG. 7B is an image of a second (or bottom) surface of a membrane device comprising a volume enhancement region for introducing high-volume samples.

Some membrane device embodiments can comprise a volume enhancement region. The volume enhancement region is configured to accept a higher volume of sample than that which can be accommodated by the sample introduction region of the membrane. The volume enhancement region can be provided by coupling the membrane device to a substrate that comprises one or more openings that become aligned with the sample introduction region(s) of the membrane. The openings are designed so has to have a larger size than the sample introduction region such that more blood can be confined by the openings and then delivered to the sample introduction region. In other embodiments, the openings can be designed in a substrate having an increased thickness as compared to the membrane, thus providing a cylindrical holding zone for higher volumes of blood. The openings are fluidly coupled with the sample introduction regions of the membrane device and thus as blood begins flowing through the features of the membrane, blood will be delivered from the openings to the sample introduction region. In some embodiments, the volume enhancement region is fabricated as part of the membrane. In other embodiments, the volume enhancement region can be a separate structural component that is coupled to the membrane device before use. An illustration of an exemplary volume enhancement region is provided by FIG. 6. FIG. 6 is an exploded perspective view of a membrane device 600 and a volume enhancement region 602. As show in FIG. 6, volume enhancement region 602 comprises three openings 604 that are positioned such that they become fluidly coupled with sample introduction regions 606. Membrane device 600 also includes lower fluidic channels 608, which are located on a second surface 610 of the membrane device, and flow-through vias 612 that deliver blood plasma and/or blood serum from the second surface back to a first surface 614 so that blood plasma and/or blood serum can be delivered to assay regions 616 via upper fluidic channels 618. FIGS. 7A and 7B show top (FIG. 7A) and bottom (FIG. 7B) images of a membrane device embodiment wherein a high volume of blood (e.g., greater than 10 μL) is introduced onto a volume enhancement region that is coupled to a membrane.

The membrane device may further comprise one or more additional features, including but not limited to, valves, an externally coupled pump, and the like. Valves can be included in membrane device embodiments using fabrication techniques. In some embodiments, the valve can be provided by modifying a fluidic channel to include a low melting polymer (e.g., PCL or another hydrophobic polymer disclosed herein), a solid oil (e.g., coconut oil, hydrogenated coconut oil, and the like), and/or wax (e.g., paraffin wax, beeswax, and the like) that can be melted using a suitable technique (e.g., a $CO_2$ laser). The valves can be actuated (that is, opened) by selectively melting the low melting polymer valve, such as by focusing a low-energy laser beam at the desired region to be melted. In yet additional embodiments, a metallic nanoparticle ink can be inkjet-printed onto a surface of a membrane to build a heater element. Such embodiments can be used to deliver a given temperature for purposes of valve actuation (e.g., having heater elements both above and below could allow for the valves to be more than just single-use), or to provide the capability to incubate a reaction or other process. The materials making up the valves can be selected to have different melting points, but it also is feasible to have a single base material in two molecular weight increments having differing melting points. The low melting polymer layer positioned above the membrane comprising the actuated valve can be selectively heated to facilitate melting of the low melting polymer layer such that the low melting polymer is able to refill the space previously occupied by the valve prior to actuation. By allowing the low melting polymer to cool, the valve can be reformed because the low melting polymer will solidify within the fluidic channel. In yet some embodiments, a two-stage valve system can be provided by using two low melting components, wherein one melts at a lower temperature than the other so that a first valve can be operated and then the second valve provided by the second higher melting component can be actuated using a higher melting temperature. For example, a two-stage valve system could involve opening the first valve at 24° C. and then further increasing the temp to 36° C. (or higher) to open the second valve using a built-in incubation component and or a laser or other method of localized heating (e.g., custom electrically-driven heaters positioned in an area near the valve material). A built-in heater could comprise coupling an etched foil silicon-rubber/polyester heater circuit to the membrane device or by inserting a NiChrome wire in the membrane device. By melting the polymer or wax, the channel is opened so that blood, blood plasma, and/or blood serum can flow through the fluidic channel into a different region of the membrane device, such as an absorption and/or assay region as described herein. In some embodiments, a layer of low melting polymer and/or wax can be added between membranes of the membrane device comprising a plurality of membranes to provide a mechanism for reclosing such valves. Solely by way of example, a layer of a low melting polymer can be included above a membrane comprising fluidic channels with valves as discussed above.

IV. Methods of Making Membrane Device Embodiments

Disclosed herein are embodiments of methods for making the membrane devices described herein.

In some embodiments, the methods can comprise depositing a hydrophobic polymer as described herein on a membrane. In some embodiments, the hydrophobic polymer can be deposited as a solution (e.g., wherein the hydrophobic polymer is dissolved in a solvent, such as toluene) or as a thin film (e.g., wherein the hydrophobic polymer is melted and then deposited as a thin film without using a solvent). Using the hydrophobic polymer, the chemical properties of the membrane can be modified such that hydrophilic membranes are converted to hydrophobic membranes (e.g., by coating the substrate or a portion thereof with the hydrophobic polymer). In such embodiments, the now-hydrophobic regions of the membrane define hydrophilic regions that are not coated with the polymer. These hydrophilic regions typically include the sample introduction region, the fluidic channels, the flow-through vias, and other regions included in the membrane device over or through which blood, blood plasma, and/or blood serum flow will occur. In yet additional embodiments, non-hydrophilic membranes can be rendered hydrophilic. For example, a non-hydrophilic membrane can be coated with the hydrophobic polymer and then a portion of the membrane comprising the hydrophobic polymer can undergo an exposure step whereby it is treated with $O_2$ plasma and/or oxygen radicals generated from $O_2$ plasma to render the treated surface hydrophilic. In some embodiments the membrane itself can be treated with an $O_2$ plasma treatment to render a membrane surface hydrophilic. Hydrophilic regions formed on a membrane by treating only a portion of the membrane (or by treating a masked membrane as described below) with the hydrophobic polymer can serve as the sample introduction region, fluidic channels, flow-through vias, and any other regions of the membrane device in which blood, blood plasma, and/or blood serum will flow or reside.

The methods can further comprise masking a membrane with a suitable masking agent (e.g., a masking tape) before or after depositing the hydrophobic polymer. In some embodiments, the membrane can be associated with mask prior to depositing the polymer and the masked membrane can then be patterned using a suitable patterning device, such as a laser cutter, plotting cutter, or even manual cutting. In some embodiments, fluidic channels and/or capillary channels can be formed using a laser cutter at a particular pulse-per-inch (or PPI), power, and speed. In some other embodiments, the PPI can range from greater than 0 to 1000, such as 500 to 1000, or 700 to 1000; the power can range from greater than 0% to 100%, such as 1% to 30%, or 5% to 15% power; and the speed can range from greater than 0% to 100%, such as 70% to 100%, such as 80% to 100%. In yet additional embodiments, sample collection regions can be formed using a laser cutter at a particular PPI, power, and speed. In some embodiments, the PPI can range from than 0 to 1000, such as 200 to 800, or 300 to 700; the power can range from greater than 0% to 100%, such as 20% to 80%, or 30% to 70% power; and the speed can range from greater than 0% to 100%, such as 70% to 100%, such as 80% to 100%. After patterning, a portion of the masking agent can be removed from the membrane and the exposed regions of the membrane can be covered with a solution of the hydrophobic polymer using any suitable technique (e.g., airbrushing, spraying, dipping, inkjet deposition, or the like), thereby rendering the unmasked regions of the membrane hydrophobic. The membrane can then be dried using an affirmative drying step where the substrate is exposed to heat, air flow, or an inert gas flow; or simply allowing the substrate to dry in ambient atmosphere. The remaining masking agent can then be removed to expose a patterned membrane device comprising hydrophilic regions.

In yet additional embodiments, membranes that are to be patterned can first be coated with a solution of the hydrophobic polymer and then patterned by cutting the desired pattern into the polymer-coated membrane (using cutting techniques described above). Alternatively, a mask with a pre-cut pattern can be attached to the polymer-treated membrane. Patterned regions of the membrane, or a masked membrane, can then be subjected to an exposure step whereby the membrane is treated with an $O_2$ plasma treatment to render the patterned regions hydrophilic, or to render regions of the masked membrane that are exposed by way of the pre-cut patterns of the mask hydrophilic.

In embodiments using an exposure step, the membrane (and any associated mask(s)) is exposed to oxygen radicals. This exposure step does not alter or damage any reagents used in an assay platform and/or an analyte capture region and thus can be used to fabricate membrane devices wherein these components are included in the membrane device. The exposure step fixes features and/or patterns on the membranes with high accuracy, even when they have been pre-treated with reagents. In particular disclosed embodiments, oxygen radicals can be generated by an oxygen plasma decontaminator, or other instrument that is capable of generating oxygen radicals. In particular disclosed embodiments, the oxygen plasma decontaminator is used at a power of 13 W Rf (fwd) and at a pressure of 0.6 Torr. These parameters, however, can be modified as needed so as to ensure sufficient exposure/fixation for different fluidic patterns and/or components. For example, flow-through vias can be made by increasing the power and exposure time (e.g., power above 13 W Rf (fwd) and exposure time longer than 5 seconds). The exposure step can be conducted for 2 seconds to 15 seconds, such as 4 seconds to 10 seconds, or 5 seconds or longer in one single exposure step or over multiple steps. Multiple steps can include exposure over more than one time interval with the same pattern mask, or more than one exposure using different mask patterns. After exposure, any masks used on the membrane are removed to reveal the patterned membrane.

Figure 8:
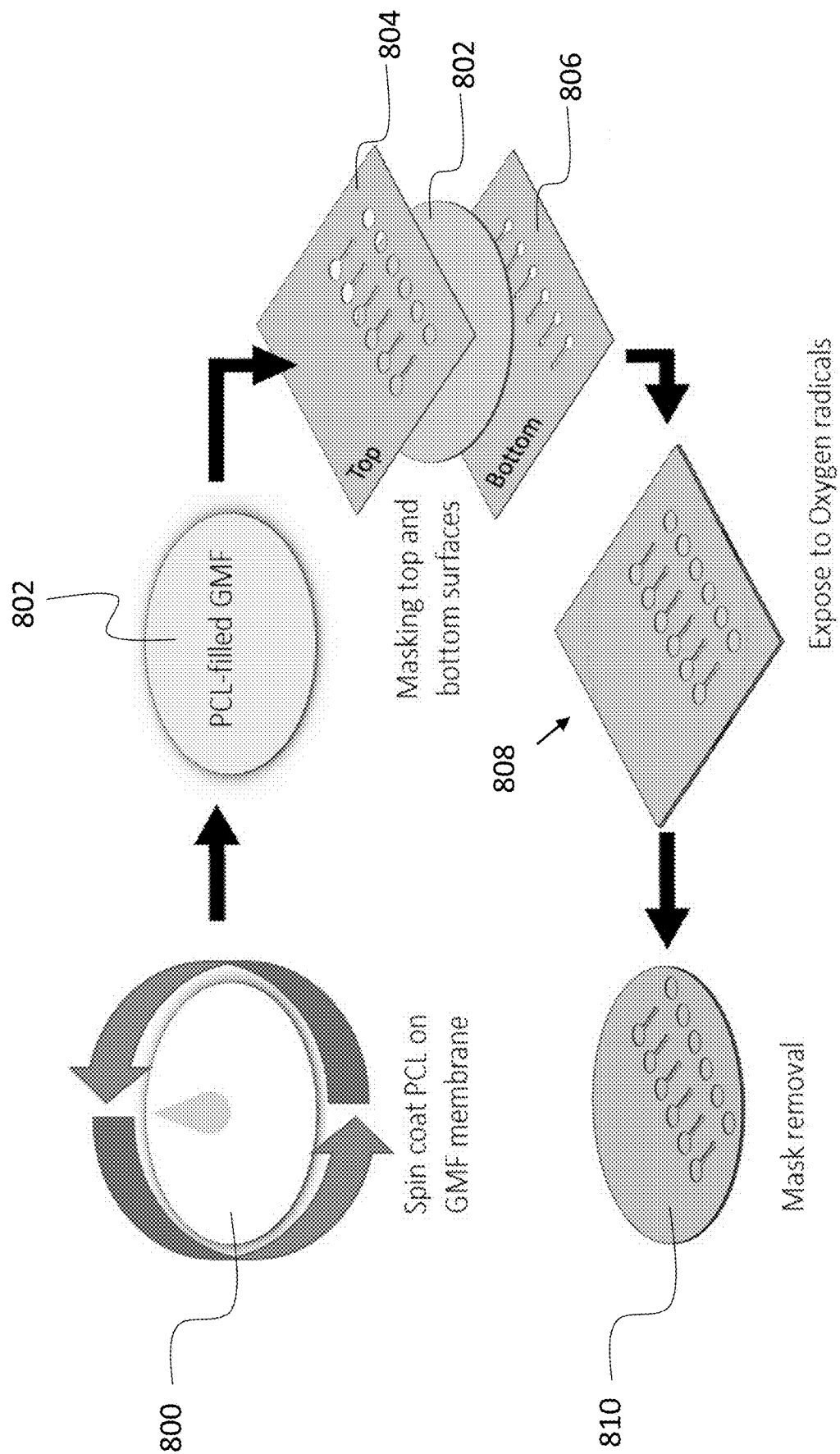
FIG. 8 is a schematic illustration of a representative method for making a membrane device according to the present disclosure.

FIG. 8 provides an illustration of a representative method of making membrane device embodiments described herein. As shown by FIG. 8, membrane 800 is coated with a polymer, such as PCL, using a spin coating method step. Polymer-treated membrane 802 is then masked with top mask 804 and bottom mask 806 to provide a template for creating sample introduction regions, flow-through vias, and fluidic channels as described herein. Masked membrane 808 is then exposed to oxygen radicals using an exposure step as described above. The masks are then removed to reveal patterned membrane 810 wherein regions of the membrane not covered by the mask are hydrophilic.

Figure 9:
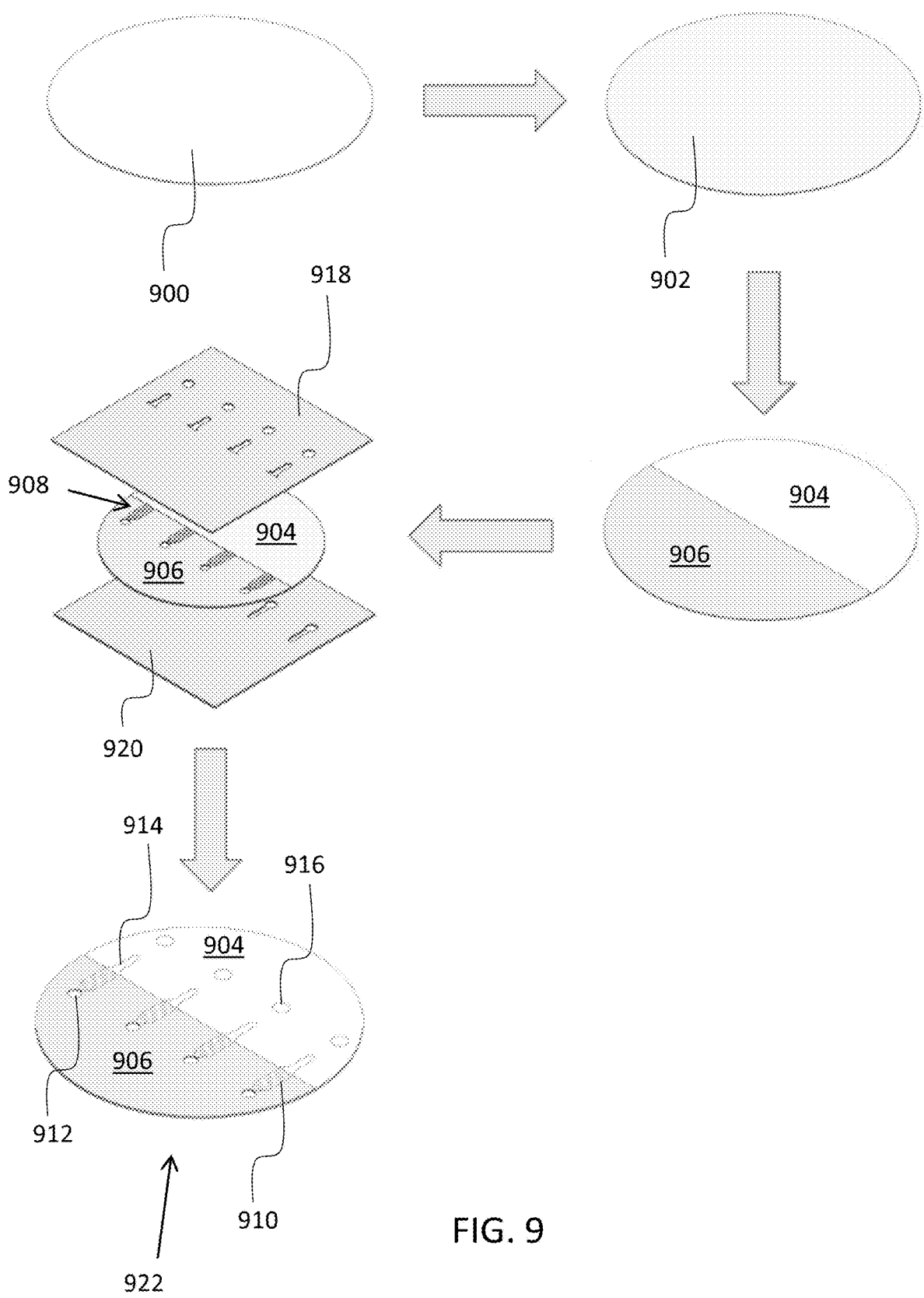
FIG. 9 is a schematic illustration of a representative method for making a membrane device comprising a wicking region and a capillary flow region.

FIG. 9 provides a schematic illustration of a representative method of making a membrane device embodiment comprising a wicking region and a capillary flow region. As illustrated in FIG. 9, uncoated membrane 900 can be coated with a first polymer to provide coated membrane 902. A portion of coated membrane 902 is then exposed to an additional polymer solution comprising a second polymer (which can be the same or different from the first polymer) at a higher concentration in the solution so that it is more viscous than the first polymer solution. This provides wicking region 904 comprising a coating of the first polymer and capillary flow region 906 comprising a coating of the first polymer and a coating the second polymer on top of the coating of the first polymer. The membrane is allowed to dry. Then, various fluidic channels, sample collection regions, sample introduction regions, and or any other structural features (e.g., assay component features) can be formed into the membrane. In some embodiments, assay reagents can be disposed in an assay region using a printer or other solution dispenser. In some embodiments, capillary channel configurations 908 can be formed in capillary flow region 906 by using a laser cutter to define the capillary channels 910. Sample collection regions 912 of capillary flow region 906 also can be formed using a laser cutter. In some embodiments, other fluidic channels (e.g., fluidic channels in wicking region 904, such as fluidic channels 914) and/or structural features (e.g., sample introduction regions 916 and flow through vias, which are not illustrated) can be formed in the membrane using a mask (e.g., masks 918 and 920) that only exposes desired areas bearing the desired component pattern (e.g., fluidic channel patterns, sample introduction regions, and the like. The membrane can be exposed to oxygen radical exposure to thereby generate the structural features defined by the mask in the membrane, thereby providing a completed device (e.g., device 922).

V. Methods of Using Membrane Device Embodiments

The membrane device embodiments described herein are used for blood analysis. The membrane device is capable of separating blood plasma and/or blood serum from whole blood based on a wicking approach. As described above, the membrane device can be integrated with many chemistries and assays to develop inexpensive point of care diagnostic membrane devices to analyze different target analytes in patients' blood plasma and/or blood serum. The membrane device can be used to analyze fresh blood or blood treated with anticoagulants enabling point of care with minimal sample preparation and use with previously collected preserved samples. As the fresh blood continues to clot on the sample introduction region of the membrane, a separate fraction flows from the sample introduction region into the flow-through via and is comprised almost entirely of serum. The separated blood plasma and/or blood serum then continues to flow through fluidic channels of the membrane device and can be delivered to different regions of the membrane device, such as an analyte capture region, an assay region, an absorption region, and any combinations thereof.

Figure 10:
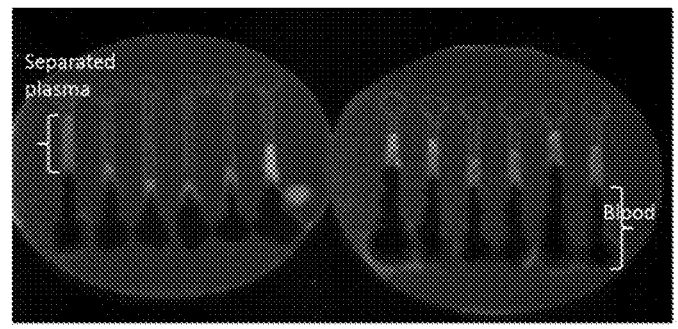
FIG. 10 is an image of a membrane device embodiment showing ultraviolet light detection of blood plasma separated from a whole blood sample.

Various different types of detection techniques can be used in combination with the membrane device embodiments described herein. In some embodiments, colorimetric detection techniques can be used to determine the concentration of different analytes in a sample. For example, in some embodiments, a colorimetric signal is produced by analytes in the sample and the intensity of this colorimetric signal can be correlated to the quantity of analyte in the solution. Intensity of the colorimetric signal can be evaluated using a suitable software program and/or quantitative analysis methods. In additional embodiments, fluorescent, phosphorescent, and/or chemiluminescent detection techniques can be used to detect the presence of analytes in a sample. Solely by way of example, a membrane device can be configured to comprise an analyte capture region wherein the membrane is functionalized with antibodies comprising a fluorophore that is either activated (that is, fluoresces) upon binding of an analyte from a sample or that is deactivated (that is, its fluorescence is quenched) upon binding of an analyte. In yet additional embodiments, blood plasma and/or blood serum that is separated from whole blood can be detected using UV irradiation, as illustrated by results shown in FIG. 10. In yet additional embodiments, a color change can occur that signals interaction between the sample and an assay reagent. In some embodiments, the color change can be observed by the naked eye, or it can be assessed using RGB color analysis. As discussed above, various different biological assays can be implemented with the disclosed membrane devices. Such biological assays are recognized by those of ordinary skill in the art with the benefit of the present disclosure. Electrochemical detection methods also can be used with membrane device embodiments described herein.

Figure 11A:
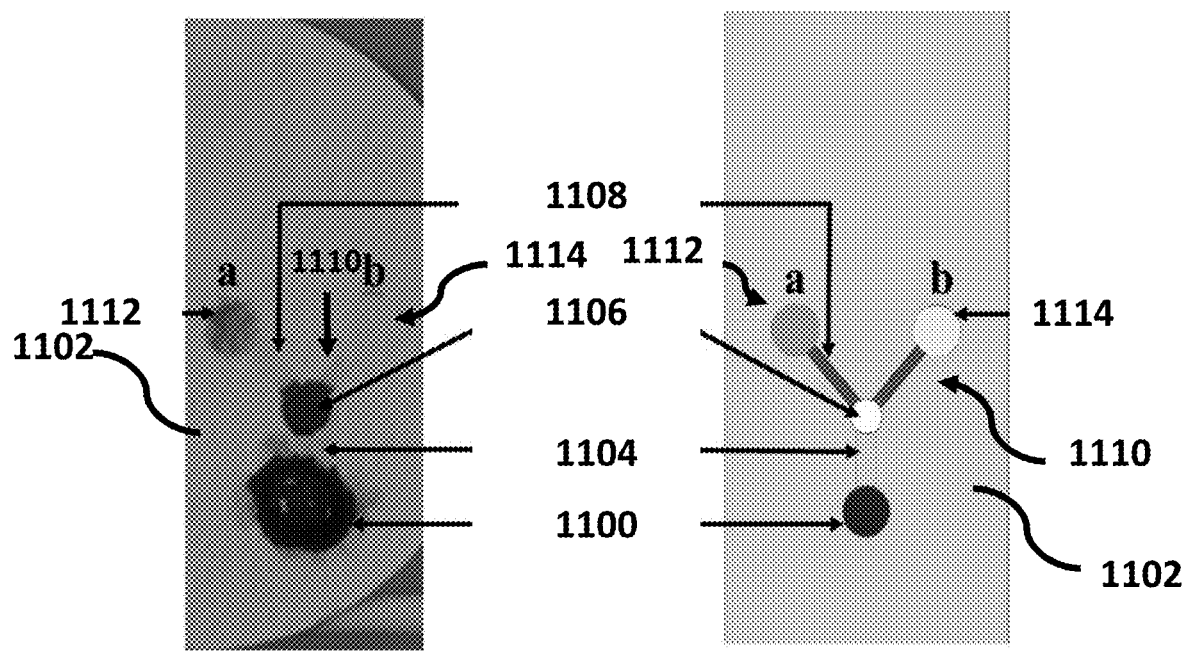
FIG. 11A is schematic illustration (right) and working example (left) of a membrane device embodiment described herein, wherein the membrane device comprises two different assay regions.
Figure 11B:
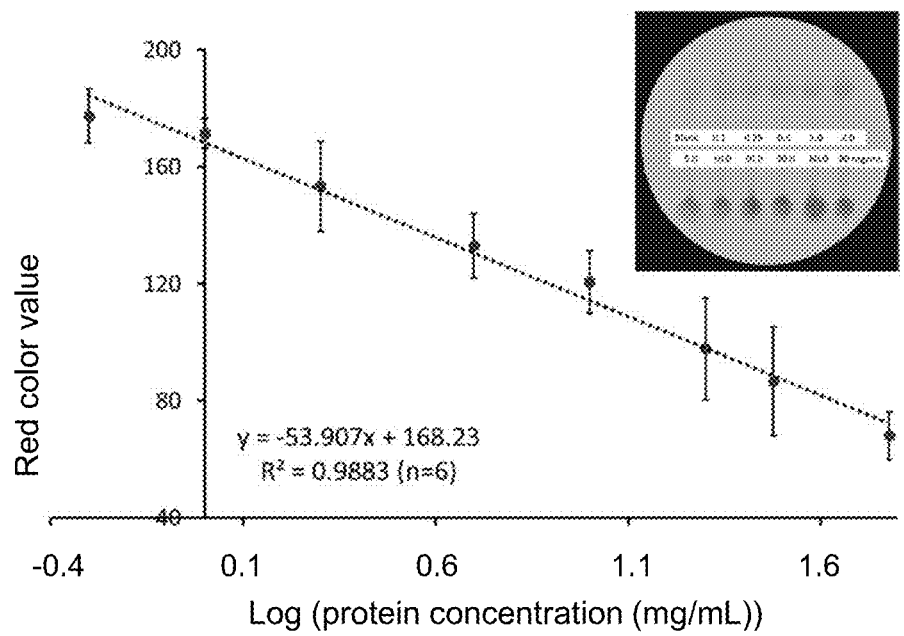
FIG. 11B is a graph of results obtained from using colorimetric detection to determine total protein concentration in an assay region of a device comprising a total protein assay platform.
Figure 11C:
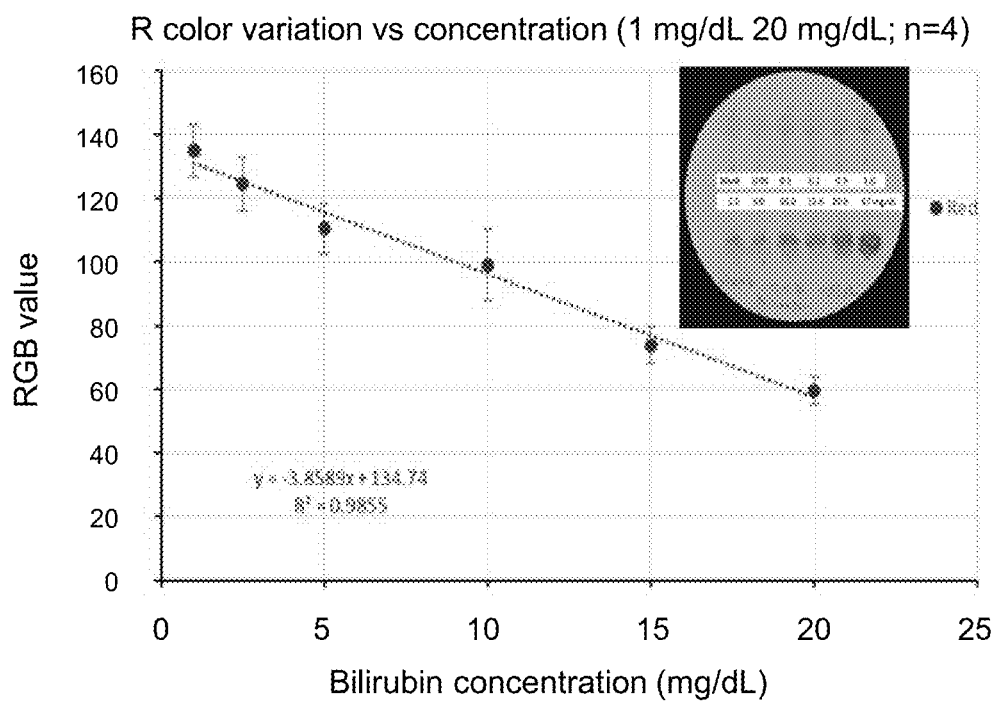
FIG. 11C is a graph of results obtained from using colorimetric detection to determine bilirubin surrogate concentration in an assay region of a device comprising a bilirubin assay platform.

A representative method of using the membrane device embodiments described herein is provided by FIG. 11A. As illustrated in FIG. 11A, whole blood can be deposited on sample introduction region 1100, which is located on a first surface 1102 of a membrane. The blood plasma and/or blood serum will pass through a flow-through via (not illustrated) to a fluidic channel 1104 positioned on a second surface (not illustrated) of the membrane. Another flow-through via 1106 can be positioned downstream of the first flow-through via and the plasma can be delivered back to the first surface 1102 of the membrane by way of flow-through via 1106. Additional fluidic channels 1108 and 1110 are included and deliver the plasma to different assay regions 1112 and 1114. Assay region 1112 can include one type of assay (e.g., a total plasma assay) and assay region 1114 can have a second different type of assay (e.g., a direct bilirubin assay). In some embodiments, a bilirubin assay composition can comprise 4-nitrobenzenediazonium salt, 5-sulfosalicylic acid, urea, EDTA-$N_2$, and 50% $H_2SO_4$ and concentrated HCl (pH<1.0). Illustrative results obtained from using a membrane device using two different assay regions are shown by FIGS. 11B and 11C. The intensity of a colorimetric signal produced by an assay region can be determined and plotted to determine the concentration of the analyte producing that signal.

Figure 12:
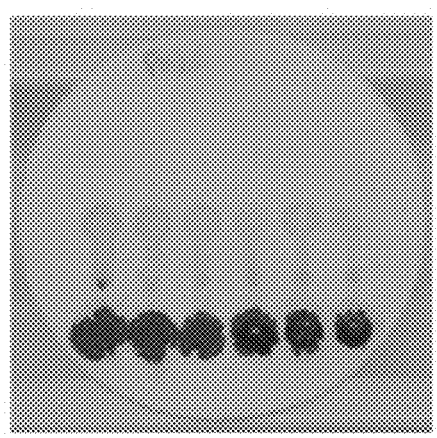
FIG. 12 is an image showing results obtained from using a membrane device comprising a sample introduction region that has been treated with fibrinogen, wherein the first (or top) surface of the membrane device is shown.
Figure 13:
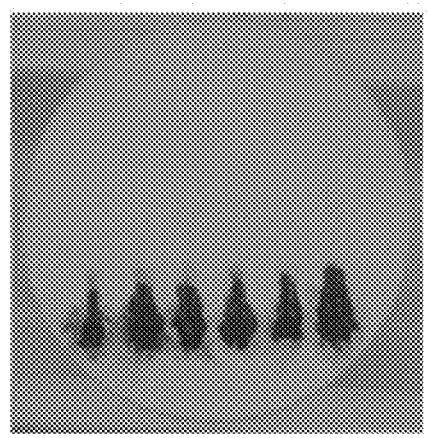
FIG. 13 is an image showing results obtained from using the membrane device of FIG. 12, wherein the second (or bottom) surface of the membrane device is shown.

In some embodiments, the sample introduction region of the membrane device can be modified to comprise a blood protein, such as fibrinogen. By depositing this blood protein in the sample introduction region, blood coagulation can be accelerated to enhance separation of plasma/serum from the whole blood. FIGS. 12 and 13 are images of results obtained using a fibrinogen-modified membrane device. FIG. 12 is an image of a first surface of the membrane and FIG. 13 is an image of a second surface of the membrane.

The membrane device embodiments of the present disclosure can be used to analyze various different types of blood samples, including samples that have been treated with an anticoagulant, human blood samples, and samples obtained from other mammals. As illustrated by FIGS. 14A and 14B, canine blood treated with ethylenediaminetetraacetic acid (EDTA) can be separated from plasma using a membrane device embodiment described herein. FIG. 14A is an image of a first surface of the membrane device and FIG. 14B is an image of a second surface of the membrane device. As seen by FIG. 14A, plasma is separated from the whole blood sample via fluidic channels and flow-through vias that have been created in the membrane. Similar results are achieved with raw canine blood as illustrated by FIGS. 15A and 15B. Additional analysis results are shown by FIGS. 16A and 16B and FIGS. 17A and 17B. FIGS. 16A and 16B are images of results showing blood plasma separation from canine whole blood treated with EDTA using a membrane device with fluidic channels that are 0.75 mm wide, wherein FIG. 16A shows a first surface of the membrane and FIG. 16B shows a second surface of the membrane. FIGS. 17A and 17B are images of results showing blood plasma separation from canine whole blood treated with EDTA using a membrane device with fluidic channels that are 1.25 mm wide, wherein FIG. 17A shows a first surface of the membrane and FIG. 17B shows a second surface of the membrane. While no flow-through via is included in the membrane devices illustrated in FIG. 16A, 16B, 17A, or 17B, one can be included.

In some embodiments, the device can be used with a syringe pump that exerts a constant aspiration force and extracts fluid from the laser-rastered collection region of certain device embodiments comprising a wicking region and a capillary flow region, while additional sample is constantly introduced into the sample introduction region in the wicking region. Furthermore, device embodiments comprising multiple wicking fluidic channels and/or capillary channels can be fabricated to feed a single sample collection region, thus multiple samples can be introduced to a single device simultaneously.

The device embodiments disclosed herein are chemically inert and compatible with many biological assays, and thus are useful in point-of-care blood diagnostics. As described herein, the device embodiments enable collection of separated plasma, which allows the device to be used as a sample preparation process prior to many blood diagnosis wet chemistries (e.g., enzyme-linked immunosorbent assay, rapid plasma reagin, *Treponema pallidum* hemagglutination assay, Vitros® slides, and the like). In yet additional embodiments, assay chemistries (pre-treatment or end assays if necessary) can be introduced to the device itself before or after the oxygen radical exposure step. Such capability allows this device to function as both an inexpensive wicking microfluidic blood sample preparation technology (for use with wet chemistries) and as a complete diagnostic device platform. Device embodiments also are compatible with various detection platforms, such as colorimetry-based platforms, fluorimetry-based platforms, and the like.

In yet additional embodiments, membrane device embodiments disclosed herein can be used for dried blood spot (DBS) testing. Such device embodiments can replace conventional DBS cards that, unlike the present membrane device embodiments, do not allow blood plasma and serum separation and preservation during sample collection. Additionally, conventional DBS cards utilize relatively low sample collection, which can yield very low target isolate masses, leading to false negatives. The membrane device embodiments disclosed herein provide the ability to tune the capacity to accommodate different volumes of a sample and further allows the user to separate blood plasma and/or serum and then drying the sample, which can pre-concentrate analytes and facilitate assay-based detection methods.

Figure 18:
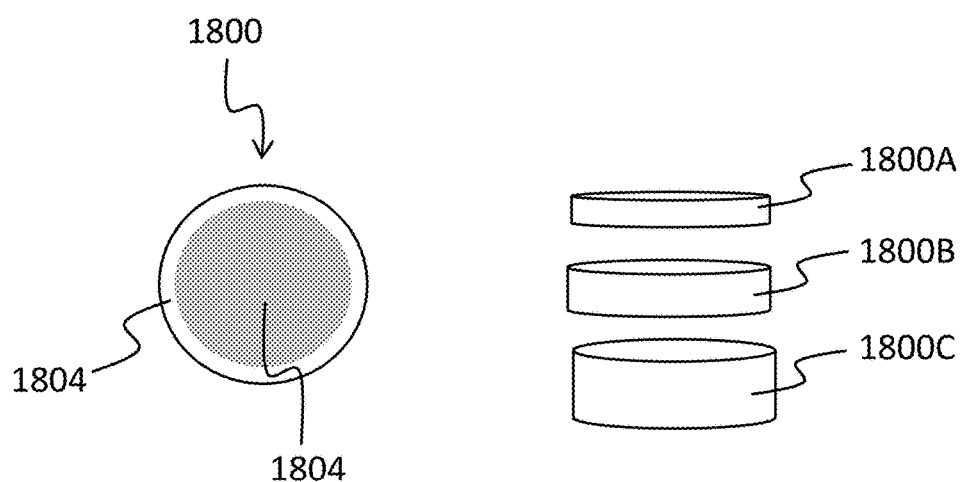
FIG. 18 is a schematic illustration of a membrane device embodiment for use in dried blood spot (DBS) testing and showing different thicknesses of the membrane device.

In some embodiments where the membrane device is used for DBS testing, the volume capacity of the membrane device can range from 5 µL (or less) to 100 µL (or more) of whole blood, which can comprise blood cells, plasma, and/or serum. In some embodiments, this can yield 2.5 to 50 µL of preserved plasma or serum. The thickness and the activated surface area of the membrane device can be modified to obtain a range of sample volumes depending on intended application. A schematic showing how sample volume can be increased by increasing the thickness of the membrane is provided by FIG. 18. As illustrated in FIG. 18, the boundary of sample introduction region 1802 is defined by hydrophobic region 1804 of membrane 1800. In some embodiments, the sample introduction region can comprise a modified surface chemistry, which can help retain the blood sample in the sample introduction region. Thickness of the membrane 1800 can be modified to allow more (e.g., see side views 1800B or 1800C) or less (e.g., see side view 1800A) sample volume as illustrated in FIG. 18.

Figure 19A:
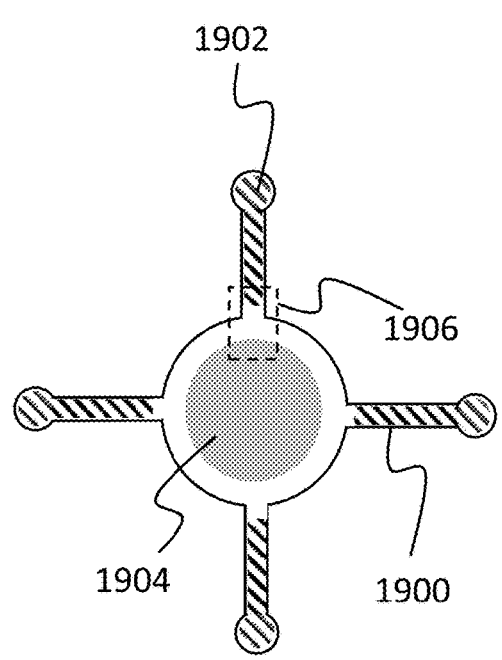
FIG. 19A is a schematic illustration of a membrane device embodiment for use in DBS which comprises fluidic channels and flow through vias for delivering a sample to four collection regions.
Figure 19B:
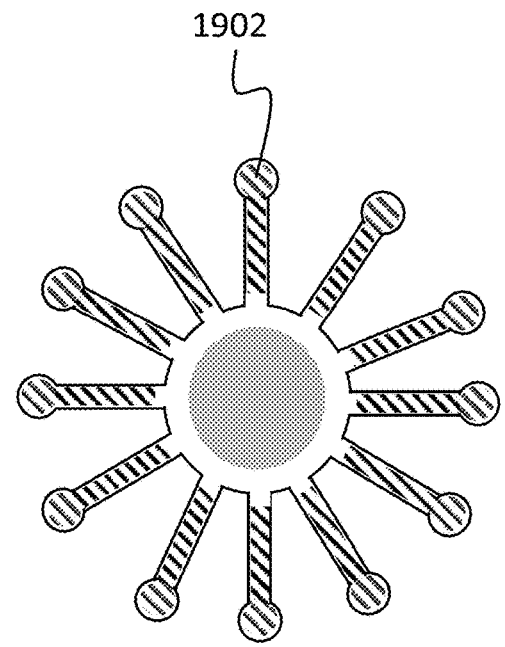
FIG. 19B is a schematic illustration of a membrane device embodiment for use in DBS which comprises fluidic channels and flow through vias for delivering a sample to eight collection regions.

Additional embodiments of the components of a membrane device that can be used in DBS testing is illustrated in FIGS. 19A and 19B. As shown in FIG. 19A, multiple fluidic channels 1900 and sample collection regions 1902 can be included that are fluidly coupled to the sample introduction region 1904. A flow through via included in region 1906 promotes the ability to separate blood plasma and/or serum from the whole blood sample and the fluidly associated channel facilitates delivery of the separated serum and/or plasma to sample collection regions 1902. Using embodiments having features illustrated in FIGS. 19A and 19B, separated blood plasma (such as in embodiments where blood treated with an anticoagulant is added to the device) or serum (such as in embodiments where fresh whole blood is added to the device) can be collected in a separate collection region that is fluidly coupled to the sample introduction region.

Figure 20A:
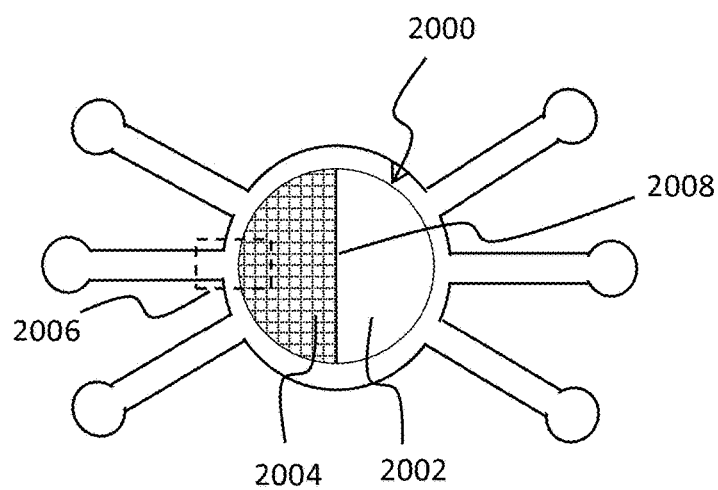
FIG. 20A is a schematic illustration of a membrane device embodiment for use in DBS which a sample introduction region that has been divided to provide the ability to separate plasma and serum components from whole blood wherein one half of the sample introduction region is treated with an anticoagulant.
Figure 20B:
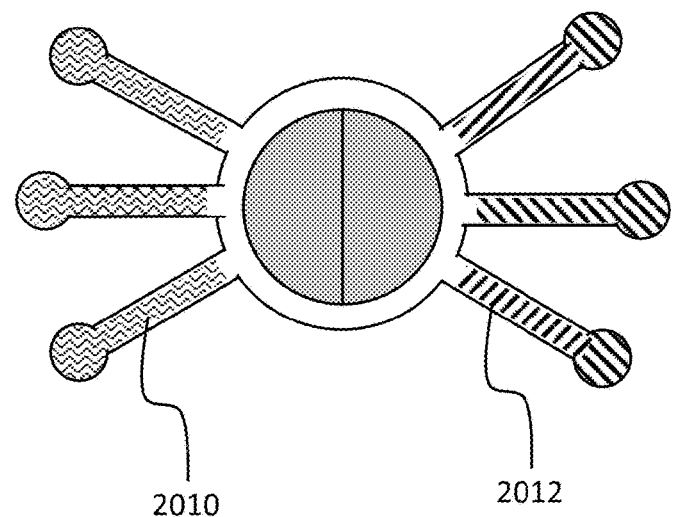
FIG. 20B is a schematic illustration of the membrane device embodiment illustrated in FIG. 20A after use and which illustrates separation of the plasma and serum components from whole blood (and from each other).

Depending on the sample volume, multiple collection regions can be connected to the same sample introduction region. In some embodiments, the blood cells are retained in the sample introduction region and, upon drying, are preserved for later analysis. When such membrane device embodiments are used with fresh blood, the fresh blood continues to clot in the sample introduction region(s), removing coagulation factors, hence, the separated fluid fraction that collects in the collection region(s) is comprised almost entirely of serum. If blood plasma separation is desired, the sample introduction region can be treated with one or more anticoagulants, as described herein, to eliminate the coagulation process, which facilitates blood plasma separation prior to drying. Therefore, embodiments of the device can be used to obtain both serum and plasma components from the same fresh blood sample as illustrated in FIGS. 20A and 20B. Upon drying of the membrane device, the membrane device can be shipped as is and the samples dried thereon can be reconstituted for use in various off-device arrays. The embodiments illustrated in FIGS. 20A and 20B show how the sample introduction region (2000) can be divided to provide one region that is untreated (e.g., region 2002) and one region that comprises an anticoagulant (e.g., region 2004). Each divided sample region is individually fluidly coupled to different collection regions through fluidic channels and a flow-through via (contained, for example, in region 2006), and allows separation of the plasma components and the serum components of the blood sample (represented by the differently shading in, for example, channels 2010 and 2012 in FIG. 20B). The regions can be divided by defining a barrier (barrier 2008) between the different regions using the hydrophobic polymer. While two regions are illustrated in FIGS. 20A and 20B, more than two regions can be defined. In some embodiments, the membrane device used for DBS testing can comprise a plurality of the configurations illustrated in FIGS. 19A, 19B, 20A, and 20B.

VI. Overview of Several Embodiments

Disclosed herein are embodiments of a membrane device, comprising: a membrane having a first surface and a second surface; a wicking region formed on the membrane, comprising a sample introduction region on the first surface of the membrane; a flow-through via that is directly and fluidly coupled to the sample introduction region and that directs fluid flow from the first surface of the membrane device to the second surface of the membrane; and a fluidic channel that is fluidly and proximally coupled to the flow-through via, wherein the fluidic channel is configured to direct fluid flow in a direction substantially perpendicular to a direction of fluid flow through the flow-through via; wherein the sample introduction region, the flow-through via, and the fluidic channel of the wicking portion are hydrophilic and are structurally defined by a first hydrophobic polymer.

In some embodiments, the device further comprises: a capillary flow region, comprising a capillary channel and a sample collection region, wherein the capillary channel is fluidly coupled to the sample collection region and further is fluidly coupled to the fluidic channel of the wicking region; wherein the capillary channel and the sample collection region are structurally defined by a second hydrophobic polymer having a concentration higher than the first hydrophobic polymer.

In any or all of the above embodiments, the capillary channel and the fluidic channel of the wicking region are positioned in an offset configuration such that fluid is able to flow from the capillary flow region to the wicking region via the capillary channel and the fluidic channel of the wicking region, but fluid is not allowed to flow from the wicking region to the capillary flow region due to the offset configuration.

In any or all of the above embodiments, the capillary flow region has a thickness that is greater than the wicking region.

In any or all of the above embodiments, the capillary flow region comprises a plurality of the capillary channels wherein each capillary channel of the plurality is fluidly coupled to the sample collection region and the fluidic channel of the wicking region.

In any or all of the above embodiments, the membrane is a hydrophilic, porous membrane comprising glass microfiber, or wherein the membrane is a hydrophobic membrane.

In any or all of the above embodiments, the membrane further comprises an additional flow-through via and the fluidic channel is distally and fluidly coupled to the additional flow-through via.

In any or all of the above embodiments, the membrane further comprises one or more additional fluidic channels that are proximally and fluidly coupled to the additional flow-through via and wherein the one or more additional fluidic channels are configured to direct blood plasma and/or blood serum flow in a direction substantially perpendicular to a direction of blood plasma and/or blood serum flow through the additional flow-through via.

In any or all of the above embodiments, the sample introduction region is fluidly coupled to a volume enhancement region that is configured to accept a higher volume of sample than that which can be accommodated by the sample introduction region.

In any or all of the above embodiments, the membrane device further comprises an assay region and the fluidic channel is distally and fluidly coupled to the assay region.

In any or all of the above embodiments, the membrane device further comprises one or more assay regions and the one or more additional fluidic channels are distally and fluidly coupled to the one or more assay regions.

In any or all of the above embodiments, the assay region comprises or is configured to accept an assay platform comprising a reagent that is selected to react with an analyte present in a sample introduced into the membrane.

In any or all of the above embodiments, the membrane device further comprises an analyte capture region that is located within the fluidic channel.

In any or all of the above embodiments, the membrane device further comprises one or more analyte capture regions that are located within the one or more additional fluidic channels.

In any or all of the above embodiments, the analyte capture region comprises an immobilized reagent capable of binding to analytes present in a sample introduced into the membrane.

In any or all of the above embodiments, the membrane further comprises an electrode and potentiometer and/or potentiostat connections electrically coupled to the electrode, wherein the fluidic channel is distally and fluidly coupled to the electrode.

In any or all of the above embodiments, the sample introduction region comprises an untreated region that does not comprise an anticoagulant and a treated region that comprises an anticoagulant and wherein the untreated region and the treated region are separated by a barrier defined by the hydrophobic polymer.

In any or all of the above embodiments, the first hydrophobic polymer is polycaprolactone having a molecular weight of 25,000 g/mol.

Also disclosed here are embodiments of a method, comprising: depositing a blood sample on the sample introduction region of a membrane according to any one or more of the above device embodiments; and analyzing a fluidic channel of the membrane, an analyte capture region of the membrane, an assay region of the membrane, or any combination thereof for the presence of an analyte in blood plasma and/or blood serum separated from the blood sample.

In any or all method embodiments, analyzing comprises (i) detecting a colorimetric signal produced in an assay region of the membrane, (ii) detecting a fluorescent, phosphorescent, or chemiluminescent signal produced in the analyte capture region of the membrane; and/or (iii) detecting quenching of a fluorescent or phosphorescent signal in the analyte capture region of the membrane.

In any or all of the above embodiments, the method can further comprise depositing a blood clotting component on the sample introduction region of the membrane prior to depositing the blood sample.

Also disclosed herein are embodiments of a method for making a device embodiment according to any one or more of the above embodiments, wherein the method comprises placing a first patterned mask on a first surface of a membrane; placing a second patterned mask on a second surface of the membrane; exposing the membrane to an exposure medium; and removing the one or more masks.

VII. Examples

Example 1

Figure 11D:
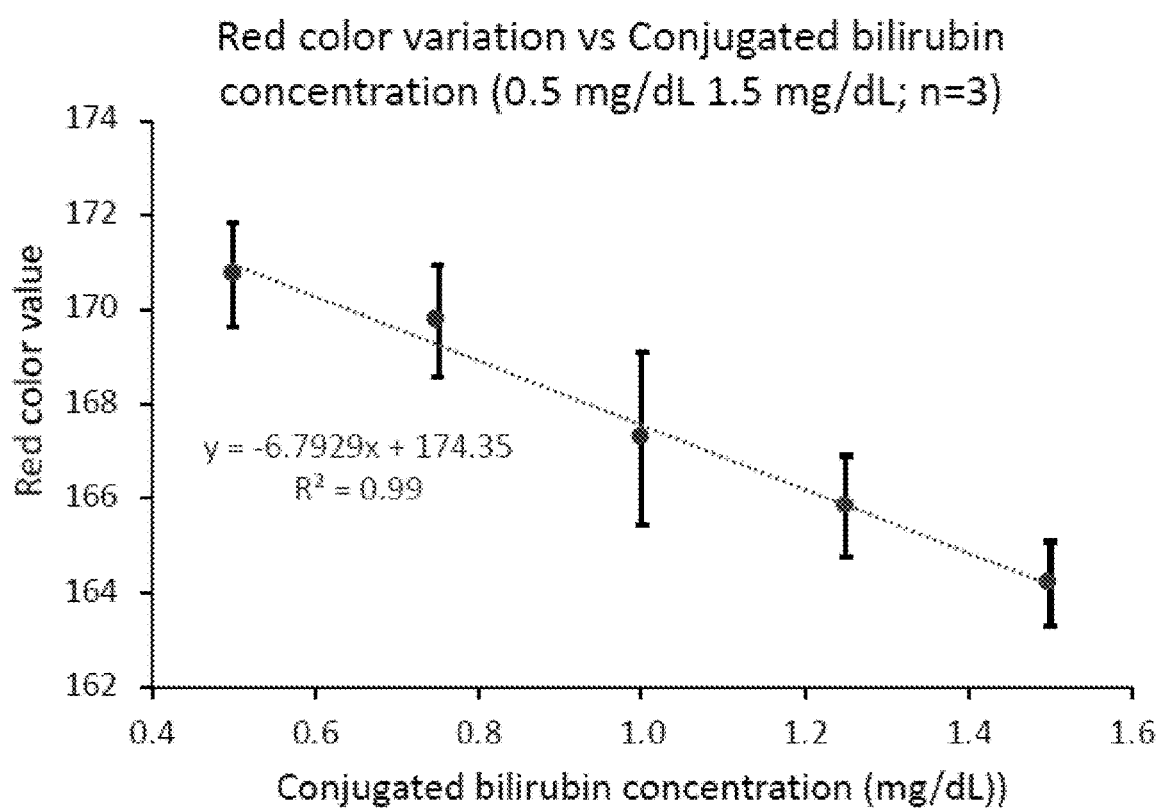
FIG. 11D is a graph of results obtained from using colorimetric detection in another embodiment to determine real bilirubin concentration in an assay region of a device comprising a bilirubin assay platform.

In this example, a membrane device with two different assay regions was evaluated. Assay reagents were mixed into a solution and dispensed using a digitally controlled device that dispenses the solution in droplets. Each assay region is a circular area with roughly 3 mm diameter made from many dispensed droplets (spots). The bilirubin assay was 1.785 µL in volume and the volume per spot was 5 nL. The total protein assay was 3.570 µL in volume and the volume per spot was 10 nL. Results from this example are illustrated in FIG. 11A. Calibration plots were prepared by obtaining a digital picture of the developed assay (shown in the inset of FIGS. 11B and 11C) and acquiring RGB color data using a free image analyzing software (ImageJ). The color data values were plotted against the concentration value (log concentration, FIG. 11B). The red channel color values had the best linear fit and were selected as the analytical parameter on both assays. Additional results from another embodiment are provided by FIG. 11D.

Example 2

Figures 21A, 21B:
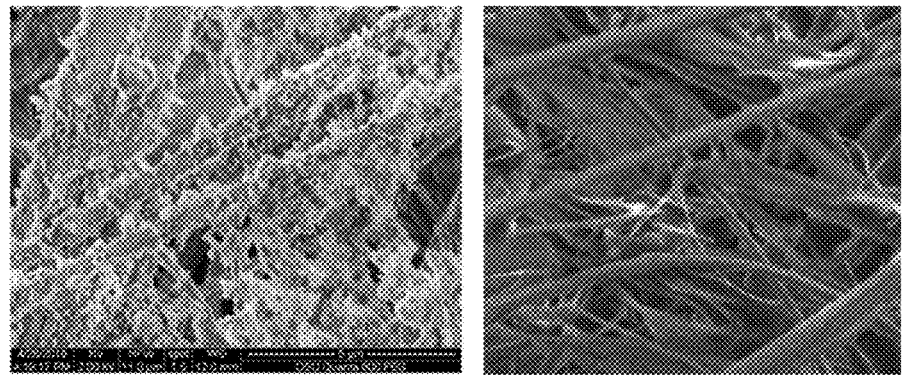
FIG. 21A is an SEM image showing interactions of a membrane's fluidic channel with fibrinogen before adding a blood sample to the membrane.
FIG. 21B is an SEM image showing interactions of the membrane of FIG. 21A after fresh blood has been deposited on the membrane, wherein nanoplates of fibrinogen disappeared after blood flow through the fluidic channel indicating that the fibrinogen interacts with the blood and/or blood plasma of the sample.
Figure 22:
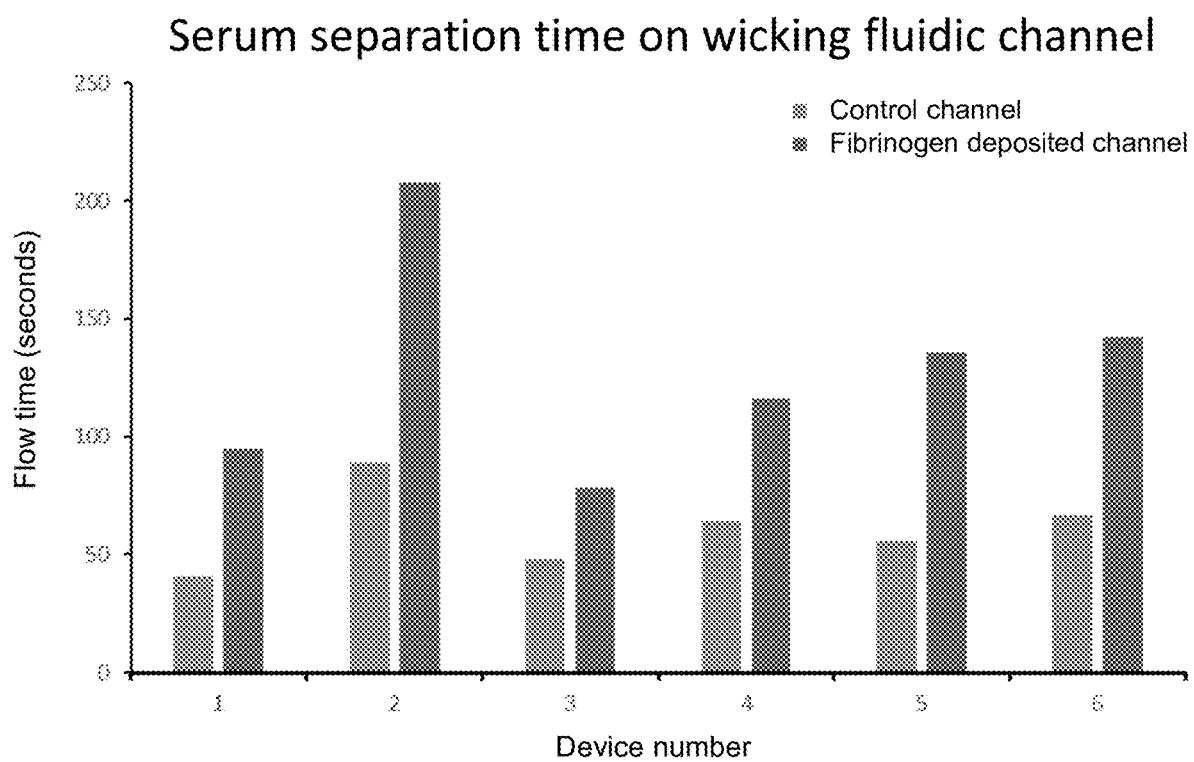
FIG. 22 is a bar chart showing a comparison of blood serum separation time for membrane devices that were not modified with fibrinogen and for membrane devices that were modified with fibrinogen.

The effect of coagulation chemistry on the bottom surface-flow channel was evaluated by testing with fresh blood. FIG. 21A shows fibrinogen nanoplates deposited on the membrane surface. After testing the membrane device with fresh blood these discrete morphologies are not visible, indicating some interaction between the fibrinogen nanoplates and fresh blood (see FIG. 21B). The time difference between the flow of the serum front and red blood cell front (serum separation time) was measured on fibrinogen deposited and control channels. In the case of a fresh blood sample, serum is separated from the blood sample—instead of plasma, which is seen with an EDTA treated blood sample. Channels deposited with fibrinogen nanoplates show a longer blood serum separation time than control channels (see FIG. 22). This is further evidence of deposited fibrinogen improving the retention of the red blood cell front on the fluidic channel.

Example 3

Figure 23:
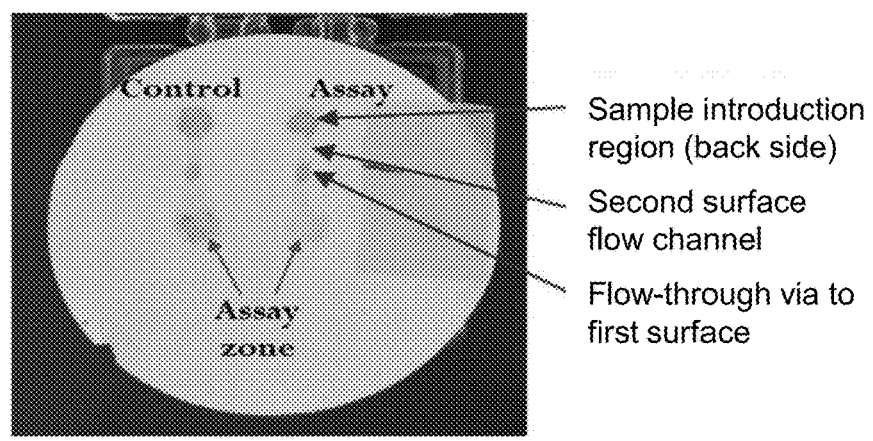
FIG. 23 is an image of a representative device wherein fluidic channels of a membrane have been modified with fibrinogen.
Figures 24A, 24B:
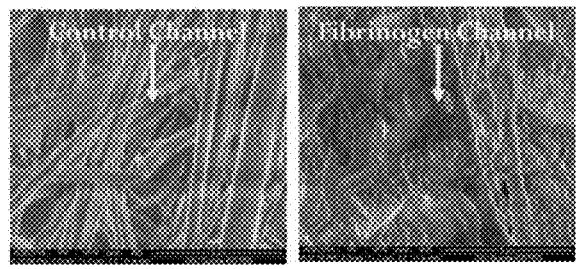
FIG. 24A is an SEM image of a sample introduction region of a membrane that has not been modified with fibrinogen but has been exposed to a non-blood fluid sample (e.g., PBS buffer) for evaluation.
FIG. 24B is an SEM image of a sample introduction region of a membrane that has been modified with fibrinogen and exposed to a non-blood fluid sample (e.g., PBS buffer) for evaluation.
Figures 24C, 24D:
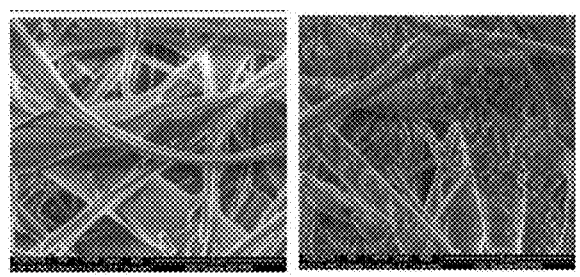
FIG. 24C is an SEM image of a fluidic channel of a membrane that has not been modified with fibrinogen but has been exposed to a non-blood fluid sample (e.g., PBS buffer) for evaluation.
FIG. 24D is an SEM image of a fluidic channel of a membrane that has been modified with fibrinogen and exposed to a non-blood fluid sample (e.g., PBS buffer) for evaluation.
Figures 24E, 24F:
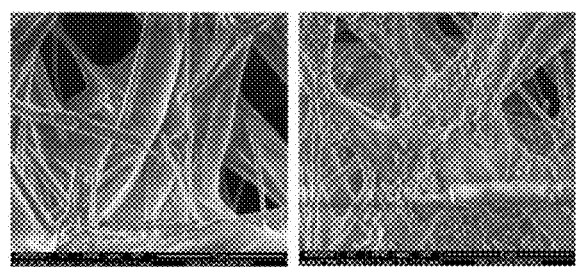
FIG. 24E is an SEM image of a flow-through via of a membrane that has not been modified with fibrinogen.
FIG. 24F is an SEM image of a flow-through via of a membrane that has been modified with fibrinogen.

Fibrinogen coated bottom-flow channels and control channels (no fibrinogen) were tested with phosphate buffered saline pH 7.4 (PBS) to evaluate both the effect of deposited fibrinogen on the fluidic channel and the effect of a non-blood liquid solution on deposited fibrinogen. Fibrinogen coated channels tested with PBS show remnant discrete morphologies suggesting that the non-blood fluid flow does not remove deposited fibrinogen. Control channels do not show these remnant morphologies, so it is unlikely they result from the PBS. The flow time of the PBS sample in the fibrinogen coated channel was comparatively longer than in the control channel. FIG. 23 shows the second (or bottom) surface of a membrane device with deposited fibrinogen after testing with PBS. FIGS. 24A-24F show images of control membrane devices having sample introduction regions, fluidic channels, and flow-through vias that do not comprise deposited fibrinogen (FIGS. 24A, 24C, and 24E) and images of membrane devices having sample introduction regions, fluidic channels, and flow-through vias that do comprise deposited fibrinogen (FIGS. 24B, 24D, and 24F).

Example 4

Figure 25:
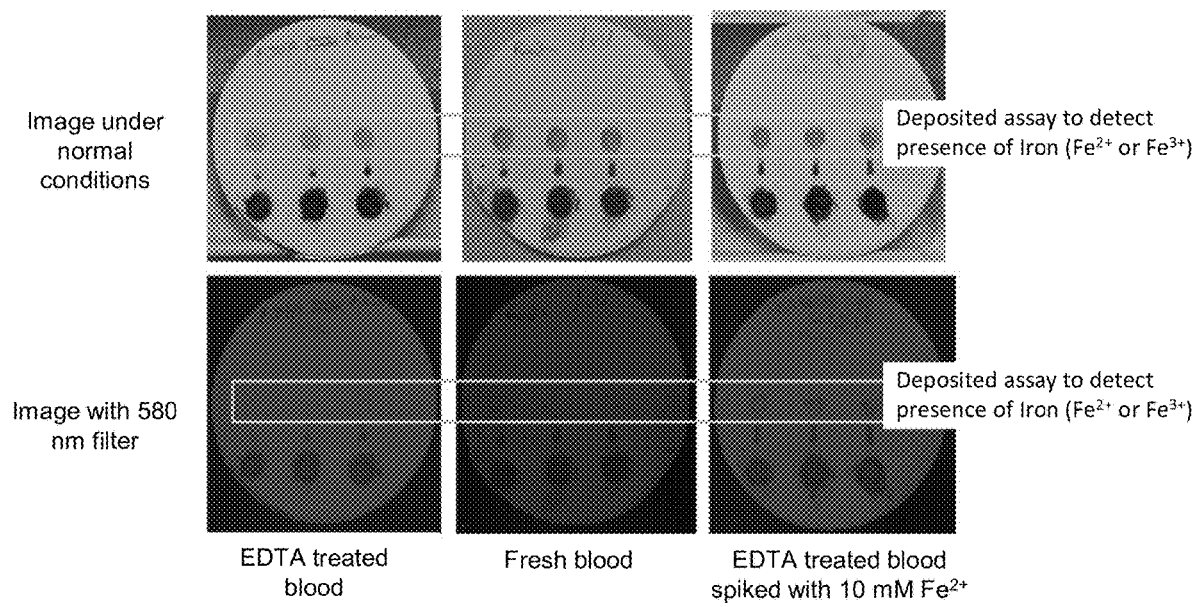
FIG. 25 is image of membrane device embodiments that are used to examine flow of iron-spiked blood samples to determine if the breakdown of red blood cells releases iron ions in the blood plasma cause any disruption in the assay reading.

Presence of iron ($Fe^{2+}$ or $Fe^{3+}$) could interfere with the assay chemistries restricting the applicability of these membrane devices. Therefore, a colorimetric assay designed to test for Iron (Fe) was immobilized on the downstream assay zone (highlighted box of FIG. 25). The membrane device was tested with fresh blood, EDTA treated blood, and EDTA treated blood spiked with 10 mM $Fe^{2+}$. The assay chemistry produces a red color precipitate which can be recognized by naked eye at higher concentrations. Using a 580 nm absorption filter, the color signal appears as a dark spot, even at low concentrations. FIG. 25 shows the dark color only appears in the membrane device tested with the $Fe^{2+}$ spiked blood sample. This suggests that the concentration of iron (which can potentially interfere with detection methods used to evaluate blood samples) that potentially reaches the assay zone through the separated plasma flow is either non-existent or is very low.

Example 5

Figures 26A, 26B, 26C:
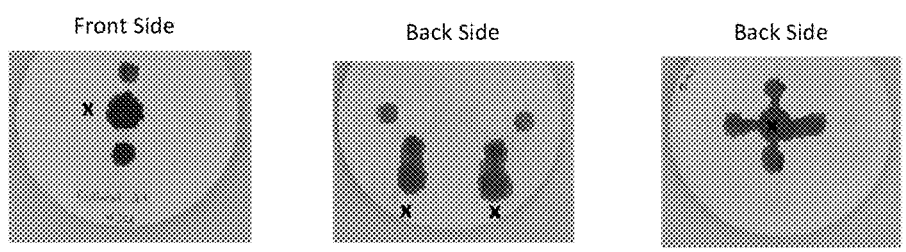
FIG. 26A is an image of a device with two assay regions opposite to a sample introduction region.
FIG. 26B is an image of the second surface (or bottom) of a membrane device with two assay regions fluidly coupled to a single sample introduction region.
FIG. 26C is an image showing the second surface (or bottom) of a membrane device with four assay regions fluidly coupled to a single sample introduction region.

As discussed herein the structural features of the membrane devices can be configured to have a plurality of patterns to facilitate blood plasma flow through the membrane device. In this example, the ability to provide different patterns was illustrated using membrane devices with different fluid flow patterns to divide the blood plasma enabling multiple assay zones on a single membrane device. Several embodiments are shown in FIGS. 26A-26C. Fluidic flow through these membrane devices was evaluated using a red dye solution.

Example 6

Figure 27:
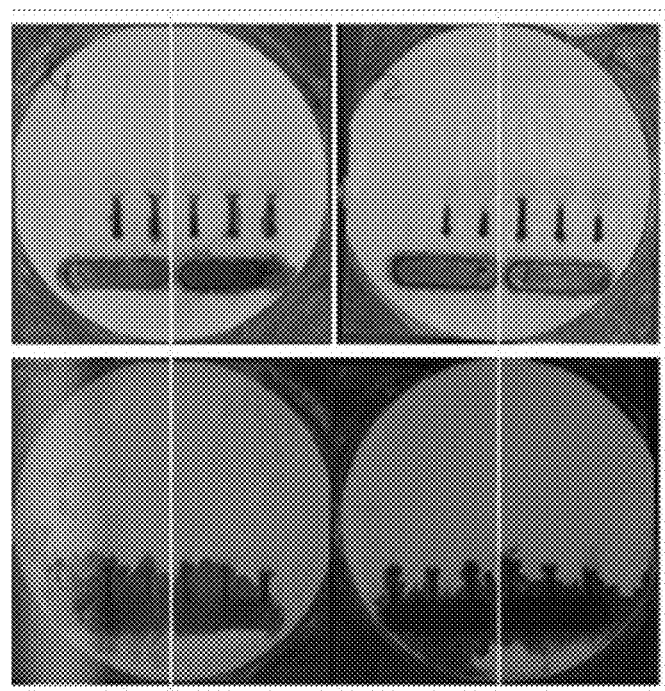
FIG. 27 is an image of a membrane device comprising a common sample introduction region that is shared with three fluidic channels, wherein the first surface (or top) of the membrane is shown in the top two images and the second surface (or bottom) of the membrane is shown in the bottom two images.
Figure 28:
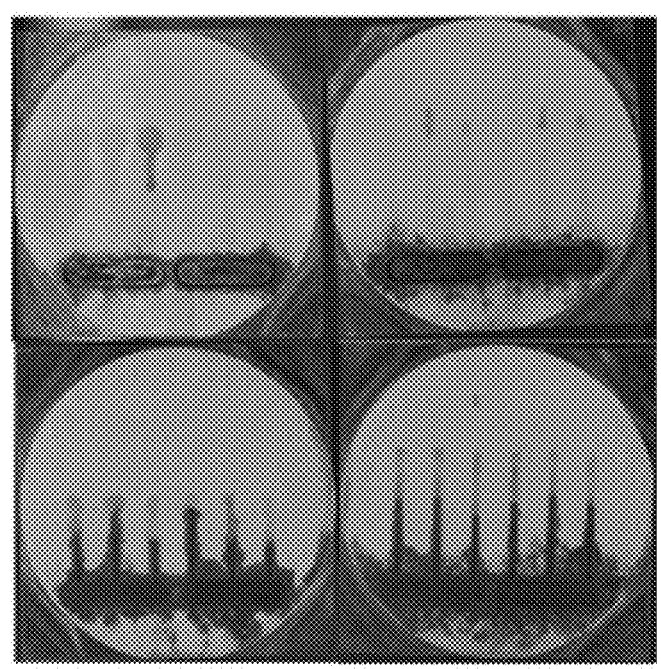
FIG. 28 is an image of membrane device embodiments comprising shorter fluidic channels (7.5 mm, top and bottom images on the left) and longer fluidic channels (top and bottom images on the right) fluidly coupled to a flow-through via that is directly and fluidly coupled to the sample introduction region.

In this example, membrane devices were fabricated with a common sample introduction region (cut-through)

designed to feed 3 separating fluidic channels. Blood plasma separation was observed on the fluidic channels, as shown by FIG. 27. While some embodiments exhibited overflow of blood into the non-patterned area of the membrane, this can be controlled using a volume enhancement region or by reducing the amount of sample added to the sample introduction region. In some embodiments using a common sample introduction region, it was determined that using a shorter bottom fluidic channel can be used to maximize separation of plasma front from red blood cell front for a given sample volume as longer bottom fluidic channels did not increase separation in some embodiments (see FIG. 28).

Example 7

Figure 29:
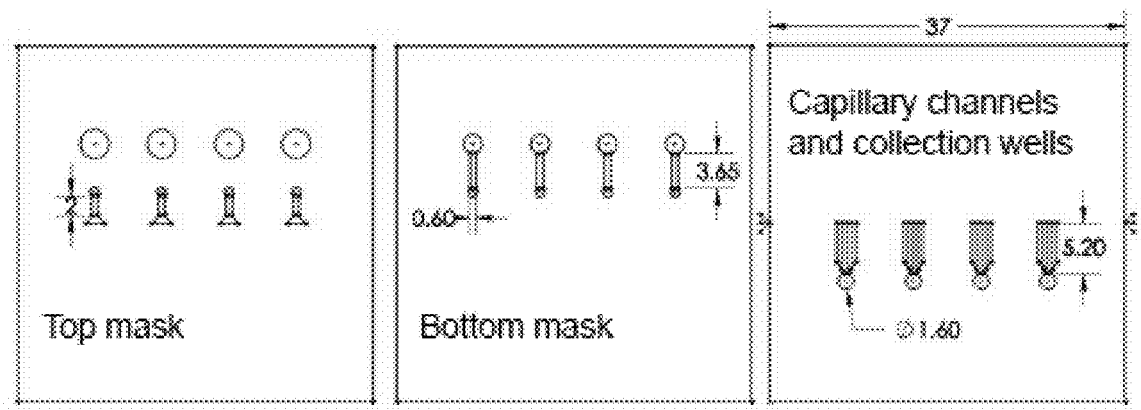
FIG. 29 shows representative embodiments of masks used to provide exemplary wicking channels, sample introduction regions, and flow-through vias in a wicking region of a device (left and middle images), as well as exemplary capillary channel and sample collection region dimensions for a capillary flow region of a device embodiment (right image).

In this example, a membrane device embodiment comprising a wicking region and a capillary flow region was prepared. The first step involved converting a hydrophilic GMF membrane to a hydrophobic membrane by filling the GMF with PCL in two steps. Initially, the GMF was spin coated with PCL of lower molecular weight and thickness to provide a layer of a first polymer, then half of this membrane was dipped into a viscous (thicker) PCL solution with a higher molecular weight to create a hard plastic portion comprising a second polymer where microscale capillary channels were cut with a laser cutter. These capillary channels guide fluid flow into a collection region, which was rastered into the device with a laser cutter. The prepared membrane was then masked using an inexpensive tape, which was cut to the desired pattern using a laser cutter. The pattern contained a flow-through via to generate a 3D fluid flow channel geometry through the membrane which enables efficient blood plasma separation. The downstream end of the plasma separator in the wicking region was connected with the laser cut features. In some embodiments, the mask can be designed to include additional features, such as multiple sample inlets and pre-treatment assay zones. The mask pattern and capillary channels were designed for the capillary flow region using drafting software and cut with a laser cutter under optimized conditions for each application. The device was placed in a face-up orientation into a homebuilt oxygen plasma exposure system and exposed to oxygen radicals for 8 seconds and then in a face down orientation for 4 additional seconds (two step exposure process). Oxygen radicals were generated under the following settings: 13 W (forward) power, 0.6 Torr pressure. The mask was removed to reveal the completed, ready-to-use device. Exemplary mask patterns are illustrated in FIG. 29.

Figure 30A:
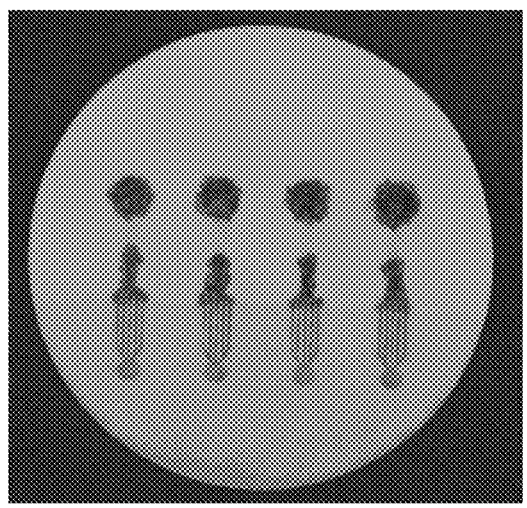
FIG. 30A is a photographic image of an exemplary device embodiment comprising a wicking region and a capillary flow region after introduction of an aqueous dye solution, wherein the device is configured to have small sample collection regions in the capillary flow region.
Figure 30B:
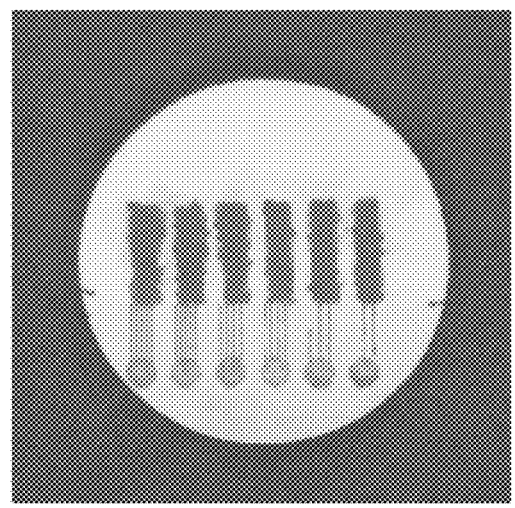
FIG. 30B is a photographic image of an exemplary device embodiment comprising a plurality of sample collection regions (in combination with other features) wherein each collection region is fluidly coupled to a different number of capillary channels.

This example was tested with aqueous dye solution. Fluid collection yields can be improved by increasing the number of capillary channels. In some embodiments, decreased collection well size concentrates the fluid into a smaller surface area, aiding in yield and ease of fluid aspiration. Employing a 3D fluid flow wicking pattern ensured that all fluid that arrives in the collection wells interacted with the device substrate (FIG. 30A), avoiding the possibility of fluid flow across the top surface of the device (FIG. 30B). In this example (FIG. 30A), 3 μL of aqueous sample volume was collected from each device with 3D fluid flow patterns out of an initial sample volume of 10 μL.

Example 8

In this example, capillary channels were fabricated using different laser cutter settings. The laser cutter settings of pulse-per-inch (PPI) for resolution, percent speed, and power were evaluated using a high power density focusing optics lens (HPDFO—Universal Laser Systems). In some embodiments, consistent channel widths without cutting through the membrane were obtained using settings of 1000 PPI, 75% speed, and 10% power. These settings were used in generating the capillary channels of the device in this example, though other settings as disclosed herein can be used. The collection wells were rastered into the device using 500 PPI, 75% speed, and 50% power (HPDFO lens). These settings generate regular features 130 micrometers wide at the top of the channel and about 60 micrometers wide at the bottom of the channel. The laser cutter settings in this example can be further modified to change the capillary channel geometries (widths, depths, etc.) for different application requirements.

Example 9

Figure 31A:
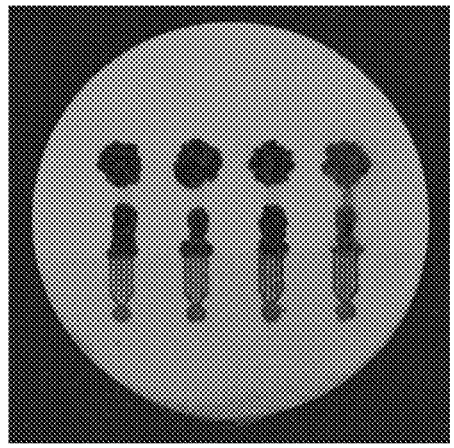
FIG. 31A is a photographic image of a membrane device embodiment used in combination with BSA protein solutions wherein the device comprises a plurality of sample collection regions, capillary channels, flow-through vias, fluidic channels, and sample introduction regions on the same device.
Figure 31B:
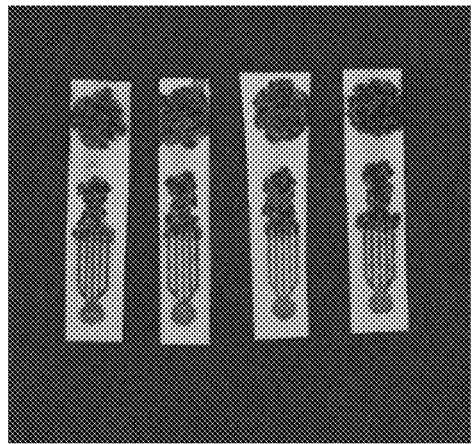
FIG. 31B is a photographic image showing a plurality of separate membrane device embodiments comprising the structural features included in the single device shown in FIG. 31A.

In this example, fluid flow through exemplary devices was tested using an aqueous dye solution. As some embodiments of the device are configured for use in blood diagnostics, further evaluations were conducted with a 70 mg/dL solution of bovine serum albumin (BSA) to mimic human blood. Results from one embodiments are shown in FIG. 31A. 1.5 μL of 70 mg/dL was collected out of an initial sample volume of 10 μL. As can be seen in FIG. 31B, isolation of fluidic features by providing separate wicking regions and capillary flow regions can improve device performance, as extra void space can be minimized when fluidic features are cut apart from the rest of the membrane. In particular examples, a pipette was used to introduce solutions into the devices and aspirate solutions from the collection wells to closely represent the real-world point-of-care diagnostic applications of the device (though it also can be used for high throughput applications).

Figure 32:
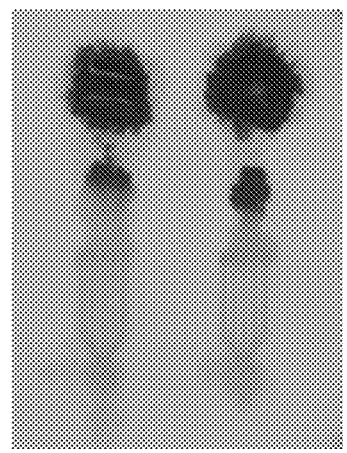
FIG. 32 is a photographic image of a device embodiment after having been used to analyze an EDTA-treated canine blood sample.

In another embodiment, a device embodiment was tested with a healthy canine blood sample (EDTA treated). About 1 μL of plasma was collected out of 10 μL of the blood introduced into the sample introduction region of the device. Protein recovery was increased to 2 μL (out of 10 μL) in one example. Since roughly half of mammalian blood is plasma by volume, this result represents a collection rate of about 20%. Results are shown in FIG. 32.

In view of the many possible embodiments to which the principles of the present disclosure may be applied, it should be recognized that the illustrated embodiments are only preferred examples and should not be taken as limiting in scope. Rather, the scope is defined by the following claims. We therefore claim as our invention all that comes within the scope and spirit of these claims.

We claim:
1. A method, comprising:
   providing a membrane device, comprising:
      a membrane having a first surface and a second surface;
      a wicking region formed on the membrane, comprising
         a sample introduction region on the first surface of the membrane; a flow-through via that is directly and fluidly coupled to the sample introduction region and that directs fluid flow from the first surface of the membrane to the second surface of the membrane; and a fluidic channel that is fluidly and proximally coupled to the flow-through via, wherein the fluidic channel is configured to direct fluid flow in a direction substantially perpendicular to a direction of fluid flow through the flow-through via;
      wherein the sample introduction region, the flow-through via, and the fluidic channel of the wicking region are hydrophilic and are structurally defined by a first hydrophobic polymer that is deposited on the first surface and/or the second surface of the membrane;

depositing a blood sample on the sample introduction region of the membrane; and detecting, quantifying, and/or qualifying an analyte in blood plasma and/or blood serum separated from the blood sample using the membrane device.

2. The method of claim 1, further comprising depositing a blood clotting component on the sample introduction region of the membrane prior to depositing the blood sample.

3. The method of claim 1, wherein the membrane is a hydrophilic, porous membrane comprising glass microfiber, or wherein the membrane is a hydrophobic membrane.

4. The method of claim 1, wherein the first hydrophobic polymer is polycaprolactone having a molecular weight of 25,000 g/mol.

5. The method of claim 1, wherein the membrane further comprises:

a capillary flow region, comprising a capillary channel and a sample collection region, wherein the capillary channel is fluidly coupled to the sample collection region and further is fluidly coupled to the fluidic channel of the wicking region, wherein the capillary channel and the sample collection region are structurally defined by a second hydrophobic polymer having a concentration higher than the first hydrophobic polymer;

an assay region, wherein the fluidic channel is distally and fluidly coupled to the assay region; and/or an analyte capture region that is located within the fluidic channel.

6. The method of claim 5, wherein detecting, quantifying, and/or qualifying comprises (i) detecting, measuring, and/or identifying a colorimetric signal produced in an assay region of the membrane, (ii) detecting, measuring, and/or identifying a fluorescent, phosphorescent, or chemiluminescent signal produced in the analyte capture region of the membrane; and/or (iii) detecting quenching of a fluorescent or phosphorescent signal in the analyte capture region of the membrane.

7. The method of claim 5, wherein the assay region comprises or is configured to accept an assay platform comprising a reagent that is selected to react with an analyte present in the blood sample.

8. The method of claim 5, wherein the analyte capture region comprises an immobilized reagent capable of binding to analytes present in the blood sample.

9. The method of claim 5, wherein the capillary channel and the fluidic channel of the wicking region are positioned in an offset configuration such that fluid from the blood sample is able to flow from the capillary flow region to the wicking region via the capillary channel and the fluidic channel of the wicking region, but fluid is not allowed to flow from the wicking region to the capillary flow region due to the offset configuration.

10. The method of claim 5, wherein the capillary flow region has a thickness that is greater than the wicking region.

11. The method of claim 5, wherein the capillary flow region comprises a plurality of the capillary channels wherein each capillary channel of the plurality is fluidly coupled to the sample collection region and the fluidic channel of the wicking region.

12. The method of claim 1, wherein the membrane further comprises an additional flow-through via and the fluidic channel is distally and fluidly coupled to the additional flow-through via.

13. The method of claim 12, wherein the membrane further comprises one or more additional fluidic channels that are proximally and fluidly coupled to the additional flow-through via and wherein the one or more additional fluidic channels are configured to direct the blood plasma and/or blood serum flow in a direction substantially perpendicular to a direction of the blood plasma and/or blood serum flow through the additional flow-through via.

14. The method of claim 13, wherein the membrane further comprises:

one or more analyte capture regions located within the one or more additional fluidic channels; and/or one or more assay regions and wherein the one or more additional fluidic channels are distally and fluidly coupled to the one or more assay regions.

15. The method of claim 1, wherein the membrane further comprises a volume enhancement region that is configured to accept a higher volume of the blood sample than that which can be accommodated by the sample introduction region and wherein the sample introduction region is fluidly coupled to the volume enhancement region.

16. The method of claim 1, wherein the membrane further comprises an electrode and potentiometer and/or potentiostat connections electrically coupled to the electrode, wherein the fluidic channel is distally and fluidly coupled to the electrode.

17. The method of claim 1, wherein the sample introduction region comprises an untreated region that does not comprise an anticoagulant and a treated region that comprises an anticoagulant and wherein the untreated region and the treated region are separated by a barrier defined by the first hydrophobic polymer.

* * * * *